United States Patent
Fandl et al.

(10) Patent No.: US 6,919,183 B2
(45) Date of Patent: Jul. 19, 2005

(54) ISOLATING CELLS EXPRESSING SECRETED PROTEINS

(75) Inventors: James P. Fandl, LaGrangeville, NY (US); Neil Stahl, Carmel, NY (US); Gang Chen, Yorktown Heights, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 59 days.

(21) Appl. No.: 10/050,279

(22) Filed: Jan. 16, 2002

(65) Prior Publication Data

US 2002/0168702 A1 Nov. 14, 2002

Related U.S. Application Data

(60) Provisional application No. 60/261,999, filed on Jan. 16, 2001.

(51) Int. Cl.[7] .................. G01N 33/53; C12N 15/09; C12N 21/02; C12N 21/08
(52) U.S. Cl. ................. 435/7.2; 435/69.3; 435/69.4; 435/69.7; 435/70.1; 435/70.2; 435/70.21; 435/70.3; 435/71.1
(58) Field of Search .................. 435/69.3, 69.4, 435/69.7, 70.1, 70.2, 70.21, 70.3, 71.1, 7.2

(56) References Cited

FOREIGN PATENT DOCUMENTS

| WO | WO 94/09117 | * | 4/1994 |
| WO | WO 99/58977 | | 11/1999 |

OTHER PUBLICATIONS

Goeddel DV. Systems for heterologous gene expression. Methods Enzymol. 1990;185:3–7.*
Lee et al. Microbial cell–surface display. Trends Biotechnol. Jan. 2003;21(1):45–52.*
Opekarova et al. Specific lipid requirements of membrane proteins—a putative bottleneck in heterologous expression. Biochim Biophys Acta. Feb. 17, 2003;1610(1):11–22.*
Manz, R., et al. (1995) Proc. Natl. Acad. Sci. USA, vol. 92, pp. 1921–1925 Immunology.
Dangl and Herzenberg (1982) J. Immunol. Methods 52:1.
Gray et al., (1995) J. Immunol. Methods 182:155.
Manz et al. 1995. PNAS 92:1921–1925.
Martel et al. (1988) J. Immunol. 141:1624.
Meng et al. (2000) Gene 242:201.
Pallavacini et al. (1989) J. Immunol. Methods 117:99.
Parks et al. (1979) PNAS 76:1962.

* cited by examiner

Primary Examiner—David Guzo
Assistant Examiner—Daniel M. Sullivan
(74) Attorney, Agent, or Firm—Valeta Gregg, Esq.

(57) ABSTRACT

A method for identifying and isolating cells which produce secreted proteins. This method is based upon a specific characteristic or the expression level of the secreted protein by transiently capturing the secreted protein on the surface of an individual cell, allowing selection of rare cell clones from a heterogeneous population. Also provided is the use of this method to generate cells which produce a desired level of secreted protein or secreted protein of a particular characteristic(s), and organisms which possess such cells. In particular, the method allows rapid isolation of high expression recombinant antibody-producing cell lines, or may be applied directly to rapid isolation of specific hybridomas, or to the isolation of antibody-producing transgenic animals. This method is applicable for any cell which secretes protein.

47 Claims, 22 Drawing Sheets

CHO K1

CHO K1 + FITC-hFc

CHO K1/hFcγRI pool + FITC-hFc

RGC3 + FITC-hFc

Figure 3

| 4SC622 | IgG Species | Cells Labeled (%) |
|---|---|---|
| − | − | 0.7 |
| + | − | 93.2 |
| + | human | 0.8 |
| + | rat | 2.0 |
| + | rabbit | (1.0) |
| + | canine | 4.8 |
| + | bovine | 92.0 |
| + | ovine | 91.7 |

RGC1

RGC1 + 4SC622

RGC1+ 4SC622 + rat IgG

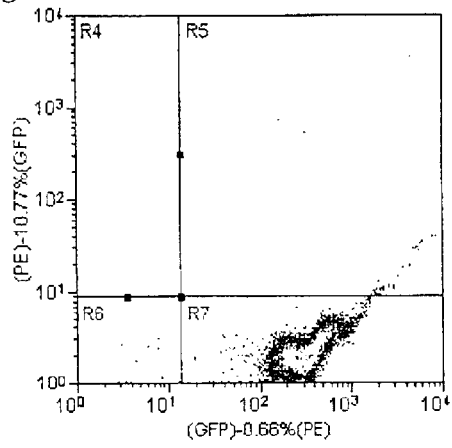
Figure 5A. RGC2
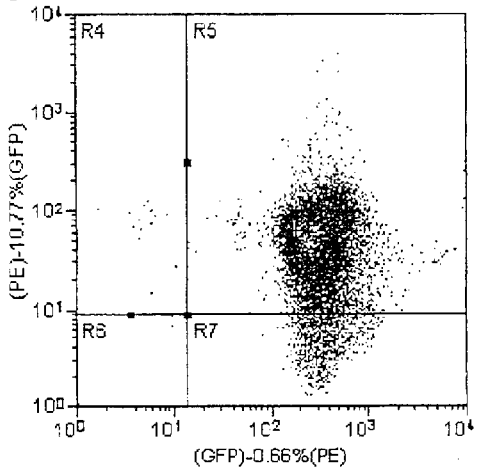
Figure 5B. RGC2 + 4SC622
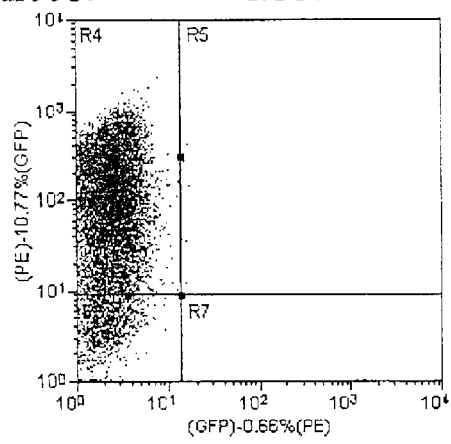
Figure 5C. RGC4
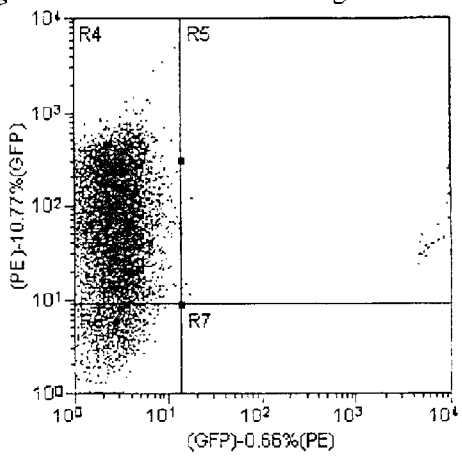
Figure 5D. RGC4 + rat IgG
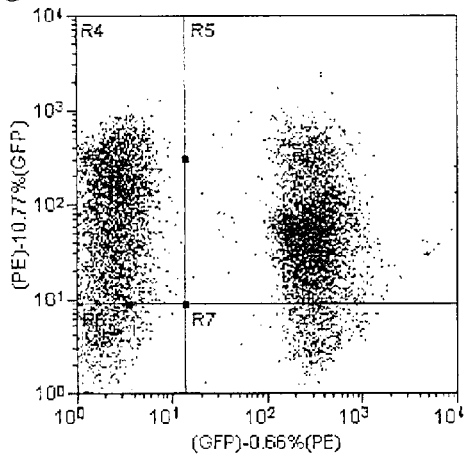
Figure 5E. RGC4 + RGC2
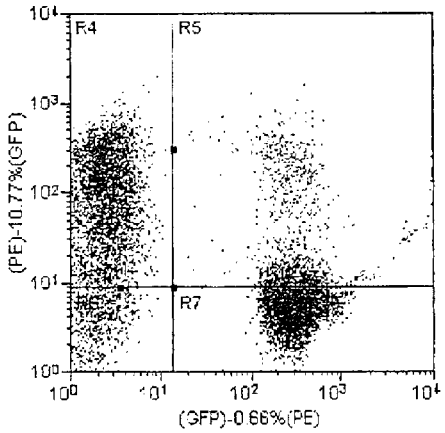
Figure 5F. RGC4 + RGC2 + rat IgG

Figure 7

| Protein | Transient ug/ml | Hand-picked CHO K1 Stable Cell Lines | | RGC1-derived Stable Cell Lines | |
|---|---|---|---|---|---|
| | | Sp.Prod. (pg/cell/day) | # clones screened | Sp. Prod. (pg/cell/day) | # clones screened |
| 4SC622 | 1.1 | 12 | 2700 | 12 | 6 |
| hVEGF-R1R2 | 33 | 68 | 190 | 77 | 62 |
| hVEGF-R1R3 | 27 | 5 | 100 | 22.6 | 42 |

Figure 8A. RGC1
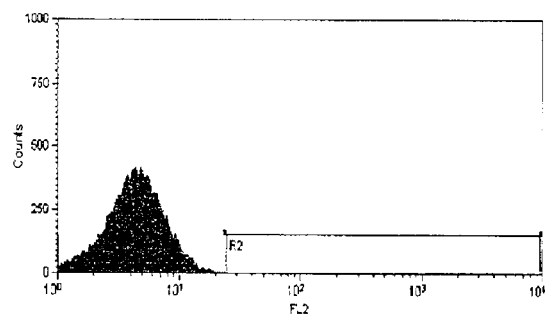
Figure 8B. RGC1 + 4SC622
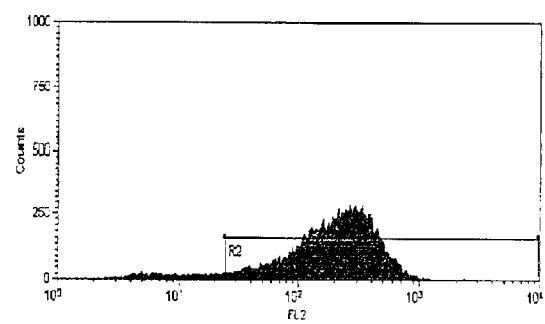
Figure 8C. RGC1 + 4SC622 + 18 hrs.
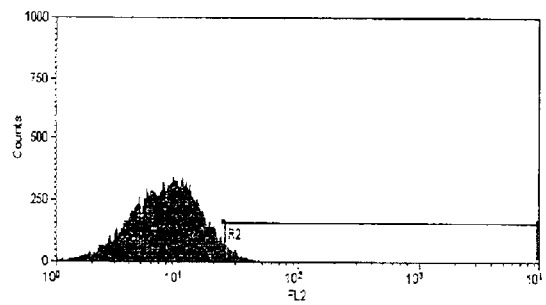

Figure 11A. CHO K1
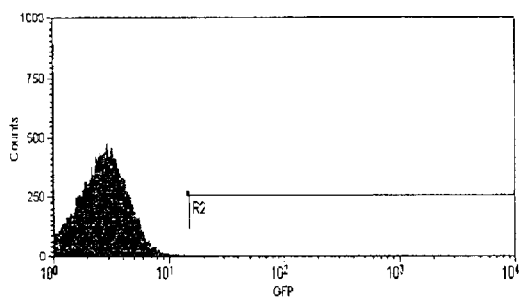
Figure 11B. RGC10 - DOX
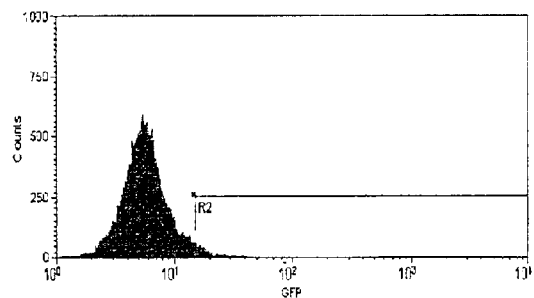
Figure 11C. RGC10 + DOX
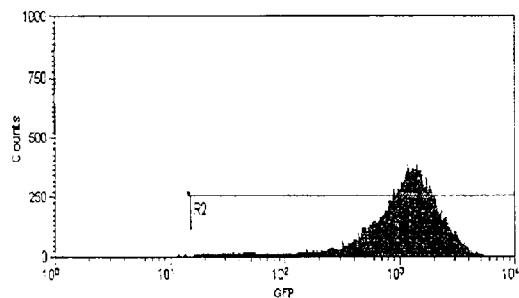

Figure 12A.  CHO K1
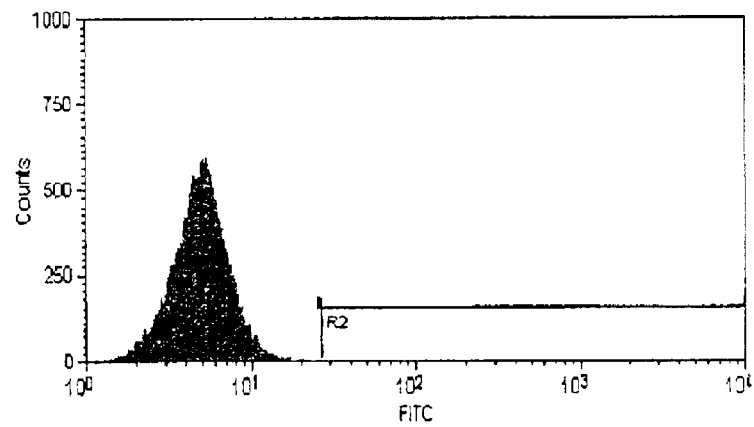
Figure 12B. RGC10/4SC622 pool-Dox
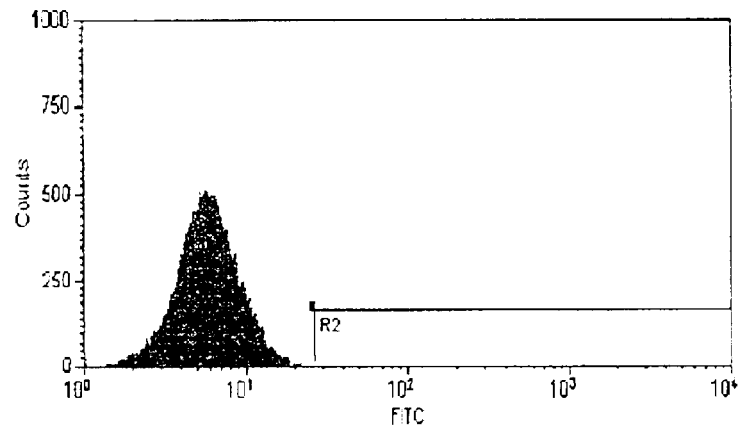
Figure 12C.  RGC10/4SC622 pool + Dox
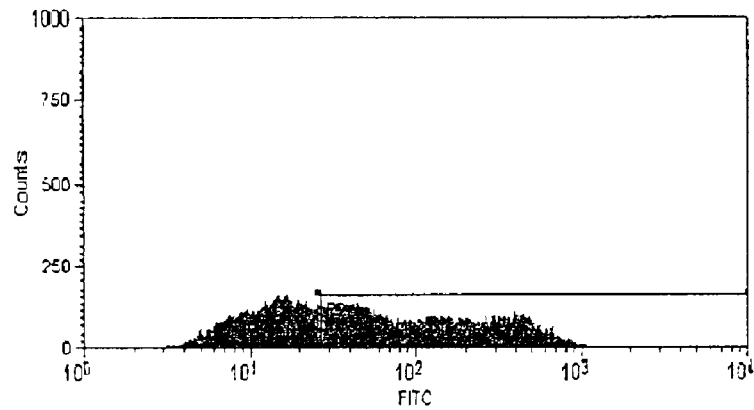

Figure 13

| Clone | Sp. Prod. | Clone | Sp. Prod. |
|---|---|---|---|
| 1A2 | 12.15 | 3A1 | 9.7 |
| 1A3 | 10.3 | 3B3 | 6.75 |
| 1B4 | 11.0 | 3B6 | 10.8 |
| 1C2 | 17.8 | 3C1 | 11.9 |
| 1D3 | 11.8 | 3C2 | 7.7 |
| 1D5 | 10.4 | 3C6 | 8.3 |
|  |  | 3D1 | 10.5 |

SP2/0

SP2/0 + Cy5-hFc

SP2/0-hFcγRI-4

SP2/0- hFcγRI-4 + Cy5-hFc

SP2/0-hFcγRI-4/4SC622 pool

SP2/0-hFcγRI-4/4SC622 pool + FITC α-hIgG

SP2/0-hFcγRI-4/4SC622 top 1% pool

SP2/0-hFcγRI-4/4SC622 top 1% pool + FITC α-hIgG

Clone 5H11

Clone 5H11 + FITC α-hIgG

RGC14

RGC14 + FITC-hFc

RGC14/pTE300 pool

RGC14/pTE300 pool + FITC-hFc

RGC18

RGC18 + FITC α-bIgG

4SC622 pool

4SC622 pool + FITC α–hIgG

SEQUENCE LISTING

<160> NUMBER OF SEQ ID NOS: 14

<210> SEQ ID NO 1
<211> LENGTH: 195
<212> TYPE: PRT
<213> ORGANISM: homo sapiens

<400> SEQUENCE: 1

| Thr | Tyr | Lys | Leu | Ile | Leu | Asn | Gly | Lys | Thr | Leu | Lys | Gly | Glu | Thr | Thr |
|---|---|---|---|---|---|---|---|---|---|---|---|---|---|---|---|
| 1 | | | | 5 | | | | | 10 | | | | | 15 | |

Thr Glu Ala Val Asp Ala Ala Thr Ala Glu Lys Val Phe Lys Gln Tyr
                20                  25                  30

Ala Asn Asp Asn Gly Val Asp Gly Glu Trp Thr Tyr Asp Asp Ala Thr
            35                  40                  45

Lys Thr Phe Thr Val Thr Glu Lys Pro Glu Val Ile Asp Ala Ser Glu
50                  55                  60

Leu Thr Pro Ala Val Thr Thr Tyr Lys Leu Val Ile Asn Gly Lys Thr
65                  70                  75                  80

Leu Lys Gly Glu Thr Thr Thr Glu Ala Val Asp Ala Ala Thr Ala Glu
                85                  90                  95

Lys Val Phe Lys Gln Tyr Ala Asn Asp Asn Gly Val Asp Gly Glu Trp
            100                 105                 110

Thr Tyr Asp Asp Ala Thr Lys Thr Phe Thr Val Thr Glu Lys Pro Glu
        115                 120                 125

Val Ile Asp Ala Ser Glu Leu Thr Pro Ala Val Thr Thr Tyr Lys Leu
    130                 135                 140

Val Ile Asn Gly Lys Thr Leu Lys Gly Glu Thr Thr Thr Lys Ala Val
145                 150                 155                 160

Asp Ala Glu Thr Ala Glu Lys Ala Phe Lys Gln Tyr Ala Asn Asp Asn
                165                 170                 175

Gly Val Asp Gly Val Trp Thr Tyr Asp Asp Ala Thr Lys Thr Phe Thr
            180                 185                 190

Val Thr Glu
        195

<210> SEQ ID NO 2
<211> LENGTH: 96
<212> TYPE: PRT
<213> ORGANISM: homo sapiens

<400> SEQUENCE: 2

Gln Val Leu Gly Leu Gln Leu Pro Thr Pro Val Trp Phe His Val Leu
1               5                   10                  15

Phe Tyr Leu Ala Val Gly Ile Met Phe Leu Val Asn Thr Val Leu Trp
                20                  25                  30

Val Thr Ile Arg Lys Glu Leu Lys Arg Lys Lys Lys Trp Asp Leu Glu
            35                  40                  45

Ile Ser Leu Asp Ser Gly His Glu Lys Lys Val Thr Ser Ser Leu Gln
50                  55                  60

Glu Asp Arg His Leu Glu Glu Leu Lys Cys Gln Glu Gln Lys Glu
65                  70                  75                  80

Glu Gln Leu Gln Glu Gly Val His Arg Lys Glu Pro Gln Gly Ala Thr
                85                  90                  95

<210> SEQ ID NO 3
<211> LENGTH: 33
<212> TYPE: DNA
<213> ORGANISM: homo sapiens

<400> SEQUENCE: 3
cgggctgatg ctgcaccaac tgtatccatc ttc                           33

-continued

<210> SEQ ID NO 4
<211> LENGTH: 33
<212> TYPE: DNA
<213> ORGANISM: homo sapiens

<400> SEQUENCE: 4
acactctccc ctgttgaagc tcttgacaat ggg                         33

<210> SEQ ID NO 5
<211> LENGTH: 31
<212> TYPE: DNA
<213> ORGANISM: homo sapiens

<400> SEQUENCE: 5
gccaaaacaa cagccccatc ggtctatcca c                          31

<210> SEQ ID NO 6
<211> LENGTH: 35
<212> TYPE: DNA
<213> ORGANISM: homo sapiens

<400> SEQUENCE: 6
tcatttaccc ggagtccggg agaagctctt agtcg                      35

<210> SEQ ID NO 7
<211> LENGTH: 47
<212> TYPE: DNA
<213> ORGANISM: homo sapiens

<400> SEQUENCE: 7
gagagtacct gcgtcatgca gatgtgaaac tgcaggagtc tggccct         47

<210> SEQ ID NO 8
<211> LENGTH: 38
<212> TYPE: DNA
<213> ORGANISM: homo sapiens

<400> SEQUENCE: 8
gagagacctg cgtcagctga ggagacggtg accgtggt                   38

<210> SEQ ID NO 9
<211> LENGTH: 35
<212> TYPE: DNA
<213> ORGANISM: homo sapiens

<400> SEQUENCE: 9
gagagggtct cacagccaaa acaacagccc catcg                      35

<210> SEQ ID NO 10
<211> LENGTH: 42
<212> TYPE: DNA
<213> ORGANISM: homo sapiens

<400> SEQUENCE: 10
gagagggtct ccggccgctc atttacccgg agtccgggag aa              42

<210> SEQ ID NO 11
<211> LENGTH: 40
<212> TYPE: DNA
<213> ORGANISM: homo sapiens

<400> SEQUENCE: 11
gagagcgtct catgcagaca tccagatgac ccagtctcca                 40

```
<210> SEQ ID NO 12
<211> LENGTH: 40
<212> TYPE: DNA
<213> ORGANISM: homo sapiens

<400> SEQUENCE: 12
gagagcgtct cacagcccgt tttatttcca gcttggtccc                                40

<210> SEQ ID NO 13
<211> LENGTH: 36
<212> TYPE: DNA
<213> ORGANISM: homo sapiens

<400> SEQUENCE: 13
gagagggtct cagctgatgc tgcaccaact gtatcc                                    36

<210> SEQ ID NO 14
<211> LENGTH: 48
<212> TYPE: DNA
<213> ORGANISM: homo sapiens

<400> SEQUENCE: 14
gagagggtct caggccgctc aacactctcc cctgttgaag ctcttgac                       48
```

ISOLATING CELLS EXPRESSING SECRETED PROTEINS

This application claims priority to U.S. provisional application No. 60/261,999, filed Jan. 16, 2001. Throughout this application various publications are referenced. The disclosures of these publications in their entireties are hereby incorporated by reference into this application.

FIELD OF THE INVENTION

The field of this invention is a method for identifying and isolating cells which produce secreted proteins. This method is based upon a specific characteristic or the expression level of the secreted protein by transiently capturing the secreted protein on the surface of an individual cell, allowing selection of rare cell clones from a heterogeneous population. The field also encompasses the use of this method to generate cells which produce a desired level of secreted protein or secreted protein of a particular characteristic(s), and organisms which possess such cells. In particular, the method allows rapid isolation of high expression recombinant antibody-producing cell lines, or may be applied directly to rapid isolation of specific hybridomas, or to the isolation of antibody-producing transgenic animals. This method is applicable for any cell which secretes protein.

Introduction

The method of the invention provides substantial advantages over current methods for isolation and identification of protein-secreting cells. The method described is more efficient, more accurate, and more broadly applicable. Specifically, any cell which secretes a protein may be isolated by the method of the invention. This aspect is particularly important as many therapeutic proteins are secreted. In addition, secreted protein-producing cells may be isolated on the basis of the protein's characteristics. For example, cells that secrete antibodies may be rapidly and conveniently isolated based on desired specificity, avidity, or isotype. Furthermore, the amount of secreted protein produced may be directly quantified, unlike many methods in the prior art wherein production of secreted protein is indirectly quantified.

The present invention thus provides for a rapid, convenient, and accurate method for systematically isolating protein-secreting cells.

BACKGROUND OF THE INVENTION

Many proteins that are of potential pharmaceutical value are secreted proteins, including growth factors, soluble receptor domains, and most importantly monoclonal antibodies. Production methods employing recombinant DNA technology to produce these and other proteins use genetic expression systems which employ host cells and expression vectors.

The expression vectors carry the gene of interest (GOI), which is to be introduced, into the cell. These expression vectors introduce genetic information, including the GOI(s), which integrate into the host cell's own genetic material. Following stable integration of the gene of interest (GOI), standard methods for isolating high expression cells may involve collection of cell pools, hand-picking colonies from plates, isolation of single cells by limited dilution, or other methods known in the art. Pools or individual clones are then expanded and screened for production of the protein of interest (POI) by direct measurement of POI activity, by immunological detection of POI, or by other suitable techniques. These procedures are laborious, inefficient, expensive, and the number of clones that can be analyzed is usually limited to a few hundred.

The large degree of heterogeneity in protein expression by cells following stable integration requires that many individual clones be screened in an effort to identify the rare integration event that results in a stable, high expression production cell line. This requirement calls for methods that enable rapid identification and isolation of cells expressing the highest level of protein production. Moreover, the collection of clone pools, or hand-picked colonies, risks losing high expression cells, which often grow more slowly, to faster growing low expression cells. Therefore, a need exists for methods that allow rapid screening and isolation of individual cells capable of high level expression of a secreted POI.

Incorporation of flow cytometry into methods used for the isolation of stable expression cell lines has improved the capability of screening large numbers of individual clones, however, currently available methods remain inadequate for diverse reasons. Early application of flow cytometry to the identification and isolation of hybridomas with a defined specificity (Parks et al. (1979) PNAS 76:1962, and Pallavacini et al. (1989) J. Immunol. Methods 117:99), isotype (Dangl and Herzenberg (1982) J. Immunol. Methods 52:1), or avidity (Jantscheff et al. (1988) J. Immunol. 141:1624) all depended on the detection of antibodies that were non-specifically bound to the cell surface. These methods assumed a correlation between the amount of surface bound and secreted antibody. Diffusion of the POI between cells of different characteristics was also a problem. Recently, two additional methods that utilize flow cytometry have been developed for the high throughput isolation of stable high expression cell lines.

The first method involves modification of the expression plasmid to include a transcriptional read out for the GOI mRNA. This is most often accomplished by inserting an internal ribosomal entry site (IRES) and a gene whose protein product is easily monitored by flow cytometry, most frequently green fluorescent protein (GFP), between the stop codon of the GOI and the terminal poly A site (Meng et al. (2000) Gene 242:201). The presence of an IRES allows the POI and GFP to be translated from the same mRNA. Therefore, the expression level of the GFP gene is indirectly related to the mRNA level for the GOI. Clones that accumulate the GFP at high levels are isolated by flow cytometry and then screened for POI production. Because this method depends on the coupling of GOI expression to the reporter gene by use of an IRES in a recombinant construction, it is not applicable to the isolation of hybridomas.

The use of flow cytometry in the isolation of expression clones allows for the rapid analysis of large numbers of clones in a high throughput format. Moreover, use of flow cytometry significantly reduces the direct handling of cells. Unfortunately, the level of GFP production is not a direct measure of the production level of the POI. Various mechanisms may uncouple the production of secreted POI from accumulation of GFP. Differences in production of the POI and the GFP reporter may result from differences in the translation efficiency of the two genes, secretion efficiency of the POI, or stability of the polycistronic mRNA.

Another method that uses flow cytometry to isolate expression clones involves encapsulation of cells within agarose microdrops (Weaver et al. (1990) Methods Enzymol. 2:234). In this method biotinylated antibodies specific for the POI are bound to the biotinylated agarose through streptavidin such that secreted POI is captured and retained within the microdrop (Gray et al., (1995) J. Immunol. Methods 182:155). The trapped POI is detected by immunostaining with an antibody specific for the POI. To reduce the encapsulating agarose from absorbing POI secreted from adjacent cells, the cells are placed in a low-permeability medium. Those cells with the highest antibody staining of the POI in the embedding agarose are identified and isolated by flow cytometry. The gel microdrop approach screens cells directly for their ability to secrete POI, rather than indirectly screening for expression of GOI mRNA, but requires the availability of suitable antibodies for trapping and staining the secreted POI and the procedure requires special equipment to generate the agarose gel microdrops. Moreover, some cells may be sensitive to the encapsulation process.

A variation of this method circumvents the requirement for embedding cells in a matrix by directly binding an antibody, specific for the POI, to the cell surface (Manz et al. 1995. PNAS 92:1921–1925). In this method, non-specific biotinylation of cell surface proteins with biotin-hydroxysuccinimide ester is followed by contact with a streptavidin-conjugated antibody capable of binding the POI. Cells secreting the POI become decorated with the POI which is then detected with an appropriately labeled second antibody. However, diffusion of POI between neighboring cells is problematic, and this method also requires a high viscosity medium to reduce diffusion of POI away from expressing cells. Because these high viscosity media are required for discriminating cells, the cells must be washed and placed in a medium suitable for cell sorting if so desired.

The problems associated with identification and isolation of high expression recombinant cell lines especially applies to the isolation of hybridomas that express an antibody of interest. However, the identification of useful hybridomas includes several additional problems; they must be screened first for antigen-binding activity, then for immunoglobulin isotype. Moreover, GFP-based methods are not applicable to the identification and isolation of hybridomas because construction of hybridomas does not include a recombinant construct such that expression of the antibody genes can be linked to a transcriptional reporter such as GFP. Hybridoma screening is a slow, laborious endeavor where the number of clones screened is limited by existing technologies.

A similar problem involves the selection of rare cells producing an antibody, an ScFv, a fragment thereof, or anything fused to an antibody constant region, with a desired specificity, isotype, and avidity for a particular antigen, from a heterogeneous population of cells expressing different antibodies, ScFvs, fragments thereof, or anything fused to antibody constant regions.

Thus a need exists for a rapid and efficient method of identifying and isolating cells expressing various secreted POIs from a large population of cells. Most desirable is a method which measures the protein expression level rather than the mRNA, as the measure of mRNA often does not accurately reflect the levels of protein which will ultimately be produced. In addition, a need exists for a more efficient method to identify cells that produce particular antibodies than what is currently available in the art.

SUMMARY OF THE INVENTION

The present invention describes a high-throughput screening method for the rapid isolation of those cells that secrete protein by directly screening for the POI. This invention also allows for the convenient monitoring of POI expression on a single-cell basis during the manufacturing process. Furthermore, this technology can be directly applied to screening of antibody producing cells.

This invention relates to the construction of cell lines that express cell surface capture molecules that bind various secreted POIs, and the use thereof to identify and isolate the cells that secrete the POI. Isolation of a cell by the methods of this invention may be based on the expression level of the POI or a specific characteristic of the POI. Through the construction or use of such a cell, any secreted protein may be captured by the cell surface capture molecule provided there is a corresponding affinity between the two.

As explained further, any molecule may be manipulated such that it can be used as a cell surface capture molecule. Therefore, this invention may be utilized to isolate any cell which secretes a protein. Furthermore, many cells may be transfected to produce secreted proteins, and therefore even cells that do not secrete proteins in their native state may be isolated as secreted protein producers through the application of this invention.

Detection of the cells with the displayed POI may be accomplished through the use of any molecule capable of directly or indirectly binding the displayed POI. Such detection molecules may facilitate the detection and/or isolation of the cells displaying the POI. In one embodiment, two molecules that bind each other and are deferentially labeled are utilized. The detection and/or isolation may be accomplished through standard techniques known in the art.

Additionally, this invention may be applied to the isolation of antibody-producing cells. Specifically, an antibody producing cell may be fused to a immortalized cell which expresses a cell surface capture molecule which binds the POI, which is an antibody in this case. The antibody-producing cell may be a B-cell or a derivative thereof, such as a plasma cell, a hybridoma, a myeloma, or a recombinant cell. The invention can also be used for isolation of cells that express desired levels, specifically high levels, of a recombinant antibody or fragments thereof. This invention also allows for the isolation of rare cells expressing an antibody, ScFv, fragments thereof, or anything fused to an antibody constant region, with a desired specificity, isotype, and avidity for a particular antigen from a population of heterologous cells expressing a library of antibody genes with varying binding specificity, isotype, and avidity. More specifically, the invention relates to the identification of antibody-producing cells that express secreted antibodies of a desired specificity and isotype, as well as antibodies that are specific for a desired epitope.

In another embodiment of the invention, transgenic animals may be created that express a cell surface capture molecule. The cells from such transgenic animal may then be screened directly for the production of the POI.

The invention also relates to a method of detecting and isolating cells that produce any secreted protein of interest (POI), comprising:

a) constructing a cell line transiently or stably expressing a cell surface capture molecule, which binds the POI, by transfecting the cell line with a nucleic acid that encodes such cell surface capture molecule;
b) transfecting said cell simultaneously or subsequently with a second nucleic acid that encodes a POI wherein such POI is secreted;
c) detecting the surface-displayed POI by contacting the cells with a detection molecule, which binds the POI;
d) isolating cells based on the detection molecule.

The invention further relates to a method of detecting and isolating cells that produce any secreted POI, comprising:

a) constructing a cell line transiently or stably expressing a cell surface capture molecule which binds the POI by transfecting with a nucleic acid that encodes such cell surface capture molecule;
b) detecting a cell from (a) that expresses said cell surface capture molecule;
c) isolating and culturing those cells detected in (b);
d) transfecting said cell in (c) simultaneously or subsequently with a second nucleic acid that encodes a POI wherein such protein is secreted;
e) detecting the surface-displayed POI by contacting the cells with (a) detection molecule(s), one or more of which binds the POI;
f) isolating cells based on the detection molecule(s).

The invention still further relates to a method of detecting and isolating cells that produce any secreted POI, comprising:

a) detecting a cell that transiently or stably expresses said cell surface capture molecule in high yield;
b) isolating and culturing those cells detected in (a);
c) transfecting said cell in (b) with a nucleic acid that encodes a POI wherein such protein is secreted;
d) detecting the surface-displayed POI by contacting the cells with (a) detection molecule(s), one or more of which binds the POI;
e) isolating cells based on the detection molecule(s).

The invention further relates to a method of detecting and isolating cells that produce any secreted POI, comprising:

a) constructing a cell line expressing a cell surface capture molecule which binds the POI by transfecting with a nucleic acid that encodes such cell surface capture molecule;
b) detecting a cell from (a) that expresses said cell surface capture molecule in high yield;
c) isolating and culturing those cells detected in (b) and allowing sufficient time for said cell to secrete the POI;
d) detecting the surface-displayed POI by contacting the cells with (a) detection molecule(s), one or more of which binds the POI;
e) isolating cells based on the detection molecule(s).

The invention relates to a non-human organism containing a cell produced by these methods. Specifically, such non-human organism may contain a cell with a cell surface capture molecule specific for antibodies.

In addition, the invention contemplates adding a membrane anchor to a protein such that it remains anchored in a cell membrane, exposed to the outside of the cell, and functions as a cell surface capture molecule. Such membrane anchor may be a transmembrane anchor or a GPI link, and may be native to the cell, recombinant, or synthetic.

The invention also embodies the addition of a signal sequence to the amino terminus of a protein, such that the protein is transported to the cell surface, and functions as a cell surface capture molecule. Such signal sequence may be native to the cell, recombinant, or synthetic.

In another embodiment, a blocking molecule which binds the cell surface capture molecule is added to reduce the diffusion of the POI from the expressing cell to a neighboring cell. In an additional embodiment, the diffusion of the POI from the expressing cell to a neighboring cell and its adherence to that cell is reduced by increasing the viscosity of the media.

This invention further relates to the identification and selection of cells that express secreted proteins including ligands, soluble receptor proteins, growth factors, and antibodies. Such secreted proteins may be recombinantly produced or naturally occurring. In addition, the nucleic acid that encodes a POI may be selected from a library, including but not limited to a cDNA library or a genomic library.

In one embodiment, such growth factors may be selected from the group consisting of Interleukin (IL)-1, IL-2, IL-4, IL-5, IL-6, IL-7, IL-9, IL-10, IL-13, IL-15, IL-16, IL-17, IL-18, IL-21, Ciliary Neurotrophic Factor (CNTF), erythropoietin, Vascular Endothelial Growth Factor (VEGF), angiopoietin 1, angiopoietin 2, TNF, Interferon-gamma, GM-CSF, TGFβ, TNF Receptor, fusion proteins, and all approved therapies made in animal cells.

In another embodiment, the antibody is selected from the group consisting of IgM, IgG, IgA, IgD or IgE, as well as various subtypes of these.

In yet another embodiment, the invention employs a ligand-specific receptor, a receptor-specific ligand, or an antibody binding protein, as the cell surface capture molecule which binds the POI. Such cell surface capture molecule may be recombinantly produced or naturally occurring.

In one embodiment, the cell surface capture molecule is a ligand-specific receptor, a receptor-specific ligand, an antibody-binding protein, an antibody, an ScFv, a fragment thereof, anything fused to a constant region of an antibody, and a peptide from a phage display or peptide library and derivatives that bind the POI. In another embodiment, the cell surface capture molecule is selected from the group consisting of Tie1, Tie2, VEGFRI (Flt1), VEGFRII (Flk1), cytokine receptor components or fusions of two or more cytokine receptor components.

In addition the invention relates to the identification of B-cells and derivatives thereof, or hybridomas that express secreted antibodies of a desired specificity, affinity or isotype. The invention can also be used for isolation of cells that express desired levels of an antibody or antibody fragments.

The invention further relates to the use of anti-immunoglobulin antibodies, anti-immunoglobulin ScFv, Protein A, Protein L, Protein G, or Fc receptor (FcR) as the cell surface capture molecule that binds the POI, wherein the POI is a secreted antibody.

BRIEF DESCRIPTION OF THE FIGURES

FIG. 3 summarizes the ability of IgG from a variety of animal species to block 4SC622 from binding to RGC1 cells.

FIG. 5A shows a flow cytometry dual parameter histogram of RGC2 cells, which express the gene for hFcγRI and GFP, stained with PE-AG184.

FIG. 5B shows a flow cytometry dual parameter histogram of RGC2 cells, which express the gene for hFcγRI and GFP, incubated with 1 ug/ml 4SC622 for 18 hours before being stained with PE-AG184.

FIG. 5C shows a flow cytometry dual parameter histogram of RGC4 cells, which express the gene for hFcγRI and 4SC622, stained with PE-AG184.

FIG. 5D shows a flow cytometry dual parameter histogram of RGC4 cells, which express the gene for hFcγRI and 4SC622, incubated with rat IgG (1 mg/ml) for 18 hours before being stained with PE-AG184.

FIG. 5E shows a flow cytometry dual parameter histogram of a mixture of RGC2, which express the gene for hFcγRI and GFP, and RGC4 cells, which express the gene for hFcγRI and 4SC622, mixed and incubated together for 18 hours prior to staining with PE-AG184.

FIG. 5F shows a flow cytometry dual parameter histogram of a mixture of RGC2, which express the gene for hFcγRI and GFP, and RGC4 cells, which express the gene for hFcγRI and 4SC622, mixed and incubated together for 18 hours with 1 mg/ml rat IgG prior to staining with PE-AG184.

FIG. 7 summarizes a comparison of the specific productivities of 4SC622 expressing cell lines. CHO K1 transiently transfected with pEE14.1-622, hand-picked stable MSX-resistant clones of CHO K1 transfected with pEE14.1-622, and MSX-resistant 4SC622 production clones isolated after transfection of RGC1 cells with pEE14.1-622.

FIG. 8A shows a flow cytometry single parameter histogram of RGC1 cells stained with PE-AG184.

FIG. 8B shows a flow cytometry single parameter histogram of RGC1 cells incubated with 1 ug/ml 4SC622 for 1 hour prior to being stained with PE-AG184.

FIG. 8C shows a flow cytometry single parameter histogram of RGC1 cells that were incubated with 1 ug/ml 4SC622 for 1 hour, then incubated in medium without 4SC622 for 18 hours prior to staining with PE-AG184.

FIG. 11A shows a flow cytometry single parameter histogram of CHO K1 cells stained with FITC-hFc.

FIG. 11B shows a flow cytometry single parameter histogram of RGC10 cells stained with FITC-hFc.

FIG. 11C shows a flow cytometry single parameter histogram of RGC10 cells induced with 1 ug/ml doxycycline for three days prior to staining with FITC-hFc.

FIG. 12A shows a flow cytometry single parameter histogram of CHO K1 cells stained with polyclonal FITC-conjugated anti-human IgG (H+L) F(ab')$_2$ fragment.

FIG. 12B shows a flow cytometry single parameter histogram of MSX-resistant RGC10 cells transfected with pEE14.1-622 and incubated with rat IgG (1 mg/ml) for 18 hours prior to staining with polyclonal FITC-conjugated anti-human IgG (H+L) F(ab')$_2$ fragment.

FIG. 12C shows a flow cytometry single parameter histogram of MSX-resistant RGC10 cells transfected with pEE14.1-622 induced with 1 ug/ml doxycycline for three days then incubated with rat IgG (1 mg/ml) for 18 hours prior to staining with polyclonal FITC-conjugated anti-human IgG (H+L) F(ab')$_2$ fragment.

FIG. 13 summarizes the specific productivities of MSX-resistant stable clones of RGC10 cells transfected with pEE14.1-622.

DETAILED DESCRIPTION OF THE INVENTION

Figure 1:
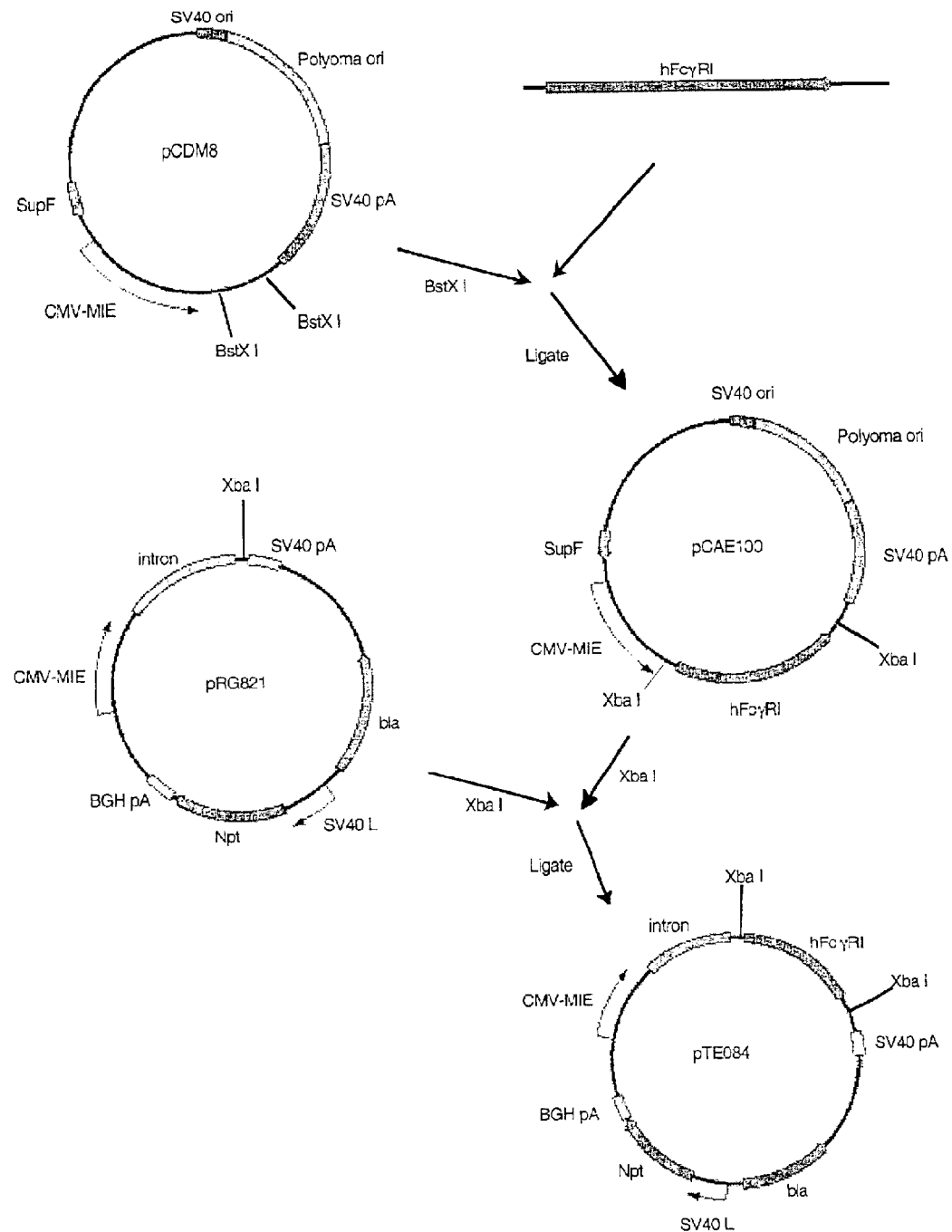
FIG. 1 represents the construction of pTE084, designed for the constitutive expression of human FcγRI from the upstream CMV-MIE promoter.

This invention describes a novel and previously unknown method of identifying and isolating the cells which produce secreted proteins. The invention is based on the production of a cell line that expresses a molecule, localized to the cell surface, which binds the POI. The cell surface-displayed POI can then be detected by labeling with various detection molecules. The amount of POI displayed on the cell surface, under specific conditions, is a direct measure of the total amount of POI secreted. POI producers may then be isolated from non-producers, and levels of production or POI characteristics may be differentiated. The advantage of the invention is that it directly quantifies the secreted POI rather than indirectly measuring the mRNA.

This invention relates to the construction or use of cells that express cell surface capture molecules which bind various secreted POIs in the same cell that produces the POI. As the cell secretes the POI, these cell surface capture molecules bind it, or complexes of POI and cell surface capture molecules may form intracellularly and then get secreted. Binding may occur in an autocrine manner or while being secreted. The cells that produce the secreted POI may then be identified and isolated. Such identification and isolation may be based on characteristics of the POI, production of the POI or lack thereof, or by specified levels of production. The cell surface capture molecule and/or the POI may be produced by the cell in its native state, or the cell surface capture molecules and/or the POI may be recombinantly produced. Through the construction or use of such a cell, any secreted protein may be captured by the cell surface capture molecule provided there is a corresponding affinity between the two. As explained further, any molecule may be manipulated such that it can be used as a cell surface capture molecule. Therefore, this invention may be utilized to isolate any cell which secretes a protein.

Most any protein has the capacity to function as a cell surface capture molecule as described by the invention. What is necessary is the ability of the desired protein to be anchored to the cell membrane and exposed to the extracellular space. If the desired cell has a signal sequence then only a membrane anchor, including but not limited to a transmembrane anchor or a GPI linkage signal, need be added to the cell surface capture molecule such that it remains anchored in the cell membrane exposed to the outside of the cell. Furthermore, if the desired protein lacks a signal sequence, a signal sequence may be added to the amino terminus of the desired protein, such that it is transported to the cell surface. A signal sequence and a membrane anchor may be native to the cell, recombinant, or synthetic.

Cells often secrete a wide variety of proteins, endogenously or following the introduction of recombinant DNA. Any secreted protein may be identified and the cell producing it may be isolated according to the method of this invention. Such secreted proteins include but are not limited to growth factors, growth factor receptors, ligands, soluble receptor components, antibodies, and peptide hormones. Such secreted proteins may or may not be recombinant. That is, the secretion of some proteins of interest from the desired cell may not require the introduction of additional nucleotide sequences. For example, the secretion of antibodies from B-cells or plasma cells is not the result of introduction of recombinant nucleotide sequences into the B-cell or plasma cell. Recombinant secreted proteins may be produced by standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, N.Y.). These secreted proteins are useful for many commercial and research purposes. This invention encompasses the production of such secreted proteins through the methodologies of the invention. Detection of the cells with the displayed POI may be accomplished through the use of any molecule capable of directly or indirectly binding the displayed POI. Such detection molecules may facilitate the detection and/or isolation of the cells displaying the POI.

The invention is applicable to the isolation of inter alia, a) ligand-producing cells by using the ligand-specific receptor as the cell surface capture molecule, b) soluble receptor-producing cells by using a surface bound receptor-specific ligand as the cell surface capture molecule, or c) antibody-producing cells by using an antibody-binding protein as the cell surface capture molecule.

In one embodiment, the invention is applicable to the isolation of ligand-producing cells by using the ligand-specific receptor as the cell surface capture molecule. More specifically, cells can be used or constructed that express a cell surface capture molecule capable of binding a growth factor or a cytokine. These cell surface capture molecule may include, but are not limited to Tie1, Tie2, VEGFRI (Flt1), VEGFRII (Flk1), cytokine receptor components or fusions of two or more cytokine receptor components. Such receptors may bind a POI, such as cytokine or a growth factor. The cytokines and growth factors may include, but are not limited to, Interleukin (IL)-1, IL-2, IL-4, IL-5, IL-6, IL-7, IL-9, IL-10, IL-13, IL-15, IL-16, IL-17, IL-18, IL-21, Ciliary Neurotrophic Factor (CNTF), erythropoietin, Vascular Endothelial Growth Factor (VEGF), angiopoietin 1, angiopoietin 2, TNF, Interferon-gamma, GM-CSF, and TGFβ.

In another embodiment, the invention is applicable to the isolation of antibody-producing cells by using an antibody-binding protein as the cell surface capture molecule. In one embodiment, an antibody producing cell may be fused to an immortalized cell which expresses a cell surface capture molecule which binds the POI which is an antibody in this case. Such antibody producing cells include but are not limited to B-cells and derivatives thereof, especially plasma cells, hybridomas (e.g. NS0), myelomas (e.g. SP2/0), recombinant cells (e.g. CHO cells expressing recombinant antibodies), or other cells producing fusion proteins consisting of antibody fragments, such as, for example, the Fc fragment from IgG. The POI may be an antibody produced by such cells which include but are not limited to IgM, IgG, IgA, IgD and IgE, as well as various subtypes of these. Cell surface capture molecules that may be used to bind antibodies include, but are not limited to, Fc receptors, such as Fc gamma RI, Fc gamma RII, Fc gamma RIII, anti-immunoglobulin antibodies, Protein A, Protein L, Protein G, and Protein H, or functional fragments thereof.

The invention, as applied to the isolation of antibody-producing cells, could be used to identify and isolate cells that express antibodies with a desired specificity, isotype, and avidity. Moreover, detection with a peptide or a protein fragment would allow identification and isolation of antibody producing cells that express antibodies specific for a desired epitope.

In accordance with the methodology of this invention, a cell is first transfected with a vector containing a nucleotide sequence that encodes a cell surface capture molecule that is capable of binding the secreted POI, under conditions in which such cell surface capture molecule is expressed. Transfected cells which are appropriate producers of such cell surface capture molecules are then detected and isolated, and such cells are cultured. These cells may either naturally produce the POI, or the POI may be recombinantly produced. If the cells naturally produce the POI, they are ready for detection and isolation. If the POI is to be recombinantly produced, then the isolated and cultured cells expressing the specified cell surface capture molecule are transfected with second nucleotide sequence that encodes the secreted POI, under conditions in which the secreted POI is expressed. Upon expression, the secreted POI binds to the cell surface capture molecules and the cells displaying bound POI are detected and isolated.

If the POI is naturally produced by the cell, the cell will not be transfected with nucleotide sequence encoding the POI. Therefore, this aspect of the invention is applicable to any and all cells producing a POI. In addition, if the cell surface capture molecule is naturally produced by the cell, the cell need not be transfected with nucleotide sequences encoding the cell surface capture molecule. Therefore, this aspect of the invention is applicable to any and all cells producing a cell surface capture molecule.

Transfection and expression are effected through the use of various vectors comprising different expression cassettes and promoters, either constitutive or regulated, and may also include enhancers, transcription terminators, splice donor and acceptor sites and other nucleotide sequences (Kaufman et al., (1991) Meth. Enzymology 185:487).

These vectors are generally commercially available or can be readily prepared by standard techniques known in the art and provide for expression in a host either by maintenance as an extrachromosomal element or by integration into the host genome. For a mammalian host, a wide variety of vectors are known based on viral replication systems, such as Simian virus, bovine papilloma virus, adenovirus, Epstein Barr Virus, retrovirus, and the like. These vectors can be used as expression vectors where transcriptional and translational initiation and termination signals are present and one or more restriction sites are available for insertion of a GOI. In addition, the vectors normally have one or more markers which allow for selection of host cells which contain the expression vector. The marker may provide for prototrophy to an auxotrophic host; biocide resistance, e.g., resistance to antibiotics, such as G418, or heavy metals, such as copper; or the like. If desired, expression vectors can be prepared by joining the various components, such as the replication system, markers, and transcriptional and translational regulatory initiation and termination signals in conjunction with the GOI. Frequently, a vector will include a prokaryotic replication system, which allows for cloning, manipulation, purification, and expansion of the desired DNA sequence.

A wide variety of transcriptional and translational regulatory sequences may be employed, depending upon the nature of the host. The transcriptional and translational regulatory signals may be derived from viral sources, such as cytomegalovirus, adenovirus, bovine papilloma virus, Simian virus, or the like, where the regulatory signals are associated with a particular gene which has a high level of expression. Alternatively, promoters from mammalian expression products, such as actin, collagen, and myosin, may be employed. Transcriptional initiation regulatory signals may be selected which allow for repression or activation, so that expression of the fused genes can be modulated. Regulatory signals may be derived from natural sources or may be chimeric in that sequences with the regulatory signal may originate from different sources.

Furthermore, the nucleic acid sequences employed for preparation of the vectors may be derived from a variety of sources. These sources include genomic DNA, cDNA, synthetic DNA, and combinations thereof. The genomic DNA may or may not include naturally occurring introns. The DNA obtained from natural sources, namely the genomic DNA or cDNA, may be obtained in a variety of ways. Host cells coding for the desired sequence may be isolated, the genomic DNA may be fragmented, conveniently by one or more restriction endonucleases, and the resulting fragments may be cloned and screened with a probe for the presence of the DNA sequence coding for the polypeptide sequence of interest. Once the cloned fragment has been identified which contains the desired DNA sequence, this fragment may be further manipulated to remove superfluous DNA, modify one or both termini, remove all or a portion of intervening sequences (introns), or the like.

Once the vector has been prepared for expression, it may be introduced into an appropriate host. Various techniques may be employed to introduce nucleic acids into host cells including, but not limited to, calcium phosphate coprecipitation, DEAE-dextran-mediated transfection, electroporation, polybrene-mediated transfection, lipid-mediated transfection, lipofection, DNA microinjection, and microprojectile-mediated gene transfer (Keown et al., (1990) Meth. Enzymology 185:527.)

The skilled artisan will be aware that well known techniques exist in the art which induce stable integration of GOI and subsequent expression of proteins to be identified and isolated for further use. Kaufman et al., ((1991) Meth. Enzymology 185:537) reviews several transformation protocols. Such techniques may utilize many different conditions including, but not limited to, various art-recognized vectors, numerous cell lines, and diverse culture conditions.

A wide variety of host cells may be transfected. These cells may be either of eukaryotic or of prokaryotic origin. The cells will often be immortalized eukaryotic cells, and in particular, mammalian cells, for example monkey kidney cells (COS), Chinese hamster ovary cells (CHO), HeLa cells, baby hamster kidney cells (BHK), human embryonic kidney cells (HEK293), leukocytes, myelomas, and embryonic stem cells. The cells may also be non mammalian cells including bacterial, fungi, yeast and insect cells, including, but not limited to, for example *Escherichia coli, Bacillus subtilus, Aspergillus* species, *Saccharomyces cerevisiae*, and *Pichia pastoris*. All cells may be grown in culture trays medium under appropriate conditions or in a synergistic host. The most desirable cells will be mammalian cells capable of culture.

The secreted POI bound to the cell surface capture molecule may be detected and isolated by various techniques known in the art. Cultures cells displaying the secreted POI may be contacted with (a) molecule(s) capable of directly or indirectly binding the secreted POI wherein such detection molecule(s) may contain a detection label, such as, for example, a chromogenic, fluorogenic, colored, fluorescent, or magnetic label. The label bound to the detection molecule may be detected and the cell isolated using various methods. Most preferably, within a cell population the label will be detected and the cell isolated utilizing flow cytometry.

Alternatively, the detection molecule may be used for the direct isolation of cells displaying the POI. This may be accomplished by conjugation of the detection molecule to a culture plate, paramagnetic molecules, or any other particle or solid support. In addition, displayed POI may be detected directly by a property of the detection molecule or the POI.

In one embodiment, two detection molecules that bind each other and are differentially labeled are used to detect a displayed secreted POI that blocks that interaction. If a cells displays a secreted POI that binds the first detection molecule and blocks the interaction between the first and second detection molecule, that cell may be isolated based on the presence of only the first detection molecule on its surface. On the other hand, if a cell displays a secreted POI that binds the first detection molecule but does not block the interaction between the first and second detection molecule, that cell may be isolated based on the presence of both detection molecules on its surface. For example, antibody producing cells expressing antibodies that specifically block, or do not block, the formation of a receptor-ligand complex may be identified. If the detection molecules are a receptor and its ligand which are differentially labeled, then an antibody producing cell that expresses antibodies that block the receptor-ligand complex from forming may be detected by the presence of one label on its surface, whereas an antibody producing cell that expresses antibodies that do not block the receptor-ligand complex from forming may be detected by the presence of both labels on its surface.

In any of the embodiments and with regards to isolating expressing cells from non-expressing cells or lesser expressing cells, one of the principal difficulties, when the POI is a secreted protein, is diffusion of POI between neighboring cells. Therefore, it is critical that any system that is designed to capture the secreted POI on the cell surface must prevent the diffusion of the POI from the expressing cell to a neighboring cell and its adherence to that cell. If diffusion is allowed to occur, and neighboring cells become decorated with the secreted POI, then separation of cells based upon the degree of POI decoration will fail to discriminate high expressing cells from cells with low expression levels, and may fail to effectively isolate expressing from non-expressing cells.

Therefore one aspect of this invention is to block the diffusion of the secreted POI between neighboring cells. This may be accomplished by the addition of a blocking molecule that binds either the cell surface capture molecule or the POI and prevents the binding of the secreted POI to the cell surface capture molecule. In this aspect, the detection molecules do not bind the blocking molecule. For example, if the cell surface receptor is the hFc gamma RI and the secreted POI possesses the human IgG Fc fragment, then diffusion of the secreted POI between neighboring cells may be blocked by the addition of exogenous rat IgG to the culture media. Detection of cells displaying secreted POI, and not bound rat IgG, is achieved by use of antibodies specific for human IgG Fc that do not recognize rat IgG.

In another aspect of this invention, binding of the secreted POI between neighboring cells is reduced by increasing the viscosity of the media.

In another aspect of this invention, the secreted POI is not allowed to accumulate in the media. This may be accomplished by regulating the expression of the secreted POI and/or the cell surface capture molecule such that brief expression of the POI results in sufficient POI to bind the cell surface capture molecule but insufficient amounts for diffusion.

In yet another aspect of this invention, cells may be removed from the media containing accumulated POI, the POI bound to the cells is stripped off, and POI expression is allowed to continue for a limited period of time such that secreted POI does not accumulate in the media. Proteins may be stripped by methods known in the art, for example, washing cells with low pH buffer.

According to this invention, those cells in a cell population that bind the most detection molecules also express the most secreted POI. In fact, the more POI that an individual cell secretes, the more POI is displayed on the cell surface. This correlation between the amount of surface-displayed POI and the expression level of the POI in that cell allows one to rapidly identify cells with a desired relative expression level from a population of cells.

In one embodiment, a DNA library may be used to express secreted protein which may be displayed on the cell surface by the cell surface capture molecule. For example, a library of DNA may also be generated from the coding regions of the antibody variable domains from B-cells isolated from immunized animals. The DNA library may then be expressed in a cell that expresses a cell surface capture molecule specific for antibodies such that clones of desired specificity, isotype, or avidity may be identified and isolated by the method of the invention.

In another embodiment, transgenic mammals may be created which express a particular cell surface capture molecule in one or more cell types. The cells from such transgenic mammals may then be screened directly for the production of a POI. For example, it may be desirable to express a cell surface capture molecule, specific for antibodies, in plasma cells. Accordingly, plasma cells from immunized mice may be harvested and those cells producing antibodies specific to the desired antigen may be isolated by the method of the invention.

In a further embodiment of the invention, antibody production is measured through the use of a CHO cell line that expresses the human Fc gamma R1 receptor (FcγRI) which binds the particular antibody that is the POI.

EXAMPLE 1

Construction of pTE084: pTE084 was constructed by ligating the 1,436 bp Xba I fragment from pCAE100 that encodes the human FcγRI (hFcγRI; GenBank accession number M21091) into the Xba I site of pRG821. The orientation of hFcγRI in desirable plasmids resulting from the ligation was examined by restriction mapping with Not I, Pst I, Eco RI, and Stu I. pTE084 was designed for the high level expression of hFcγRI, the high affinity cell surface receptor for the Fc domain of human IgG. It contains two independent expression cassettes. One cassette is a hFcγRI gene driven by the CMV-MIE promoter, and the second cassette is the neomycin phosphotransferase II (npt) gene, which confers resistance to G418, driven by the SV40 late promoter.

Figure 2A:
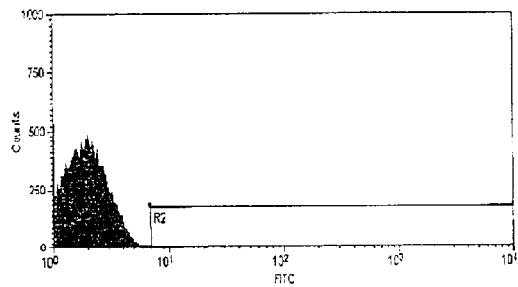
FIG. 2A shows a flow cytometry single parameter histogram of unstained CHO K1 cells.
Figure 2B:
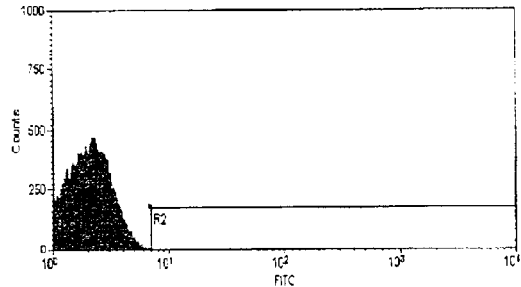
FIG. 2B shows a flow cytometry single parameter histogram of FITC-hFc stained CHO K1.
Figure 2C:
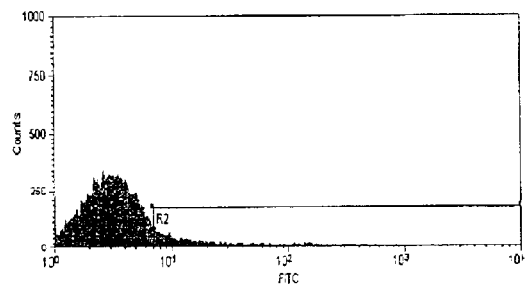
FIG. 2C shows a flow cytometry single parameter histogram of FITC-hFc stained G418-resistant CHO K1 cell pool after pTE084 transfection.
Figure 2D:
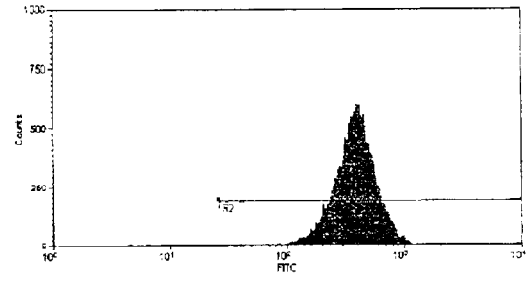
FIG. 2D shows a flow cytometry single parameter histogram of FITC-hFc stained RGC3 cells.

Construction of a CHO K1 Derivative that Expresses hFcγRI:

CHO K1 cells ($4 \times 10^6$) were transfected with pTE084 using Lipofectamine™ (Life Technologies; Rockville, Md.) following manufacturer's suggestions. The cells were placed in the culture medium (10% fetal bovine serum, 90% Ham's F-12, 2 mM L-glutamine; all reagents were from Life Technologies, Rockville, Md.) containing 500 ug/ml G418 (Life Technologies) for 15 days. The cells that survived G418 selection were trypsinized, pooled, and stained with FITC-conjugated human IgG, Fc fragment (FITC-hFc; Jackson ImmunoResearch Laboratories, West Grove, Pa.). Briefly, the cells grown on 10 cm culture plates were washed once with Dulbecco's phosphate-buffered saline (PBS) without calcium chloride and magnesium chloride (Life Technologies). Three mls of 0.25% trypsin (Life Technologies) was added to each plate. The plates were swirled until the cells detached from the plate. 10 ml culture medium was immediately added to each plate of the detached cells. The cells were then collected by centrifugation at 1,000×g for 4 minutes. After removal of supernatant, the cells were resuspended in 4 ml of 2 ug/ml FITC-hFc diluted in culture medium. The cells were then placed on a platform shaker and stained for one hour at room temperature. To remove unbound FITC-hFc, the cells were washed twice with 20 ml PBS. The degree of FITC-hFc label on the cells was measured by flow cytometry on a Moflo cell sorter (Cytomation; Fort Collins, Colo.). The FITC-hFc did not stain mock-transfected parental CHO K1 cells (FIGS. 2A and 2B) but gave rise to a distribution of fluorescence in the G418-resistant, pTE084-transfected pool (FIG. 2C). The top 1% most fluorescent cells from the selected pool were placed into 96-well plates at 1 cell/well by flow cytometry. Nine days later, 88 cell clones in the 96-well plates were expanded into 24-well plates. After 3 days, the cells in individual wells were washed once with 1 ml PBS, stained with 0.5 ml of 2 ug/ml FITC-hFc for 1 hour, washed twice with 1 ml PBS and examined for cell surface staining under a fluorescent microscope. The thirty three most fluorescent clones were chosen, expanded, then screened by flow cytometry. The FITC-hFc staining of one such clone, RGC3, was shown in FIG. 2D.

Figure 4A:
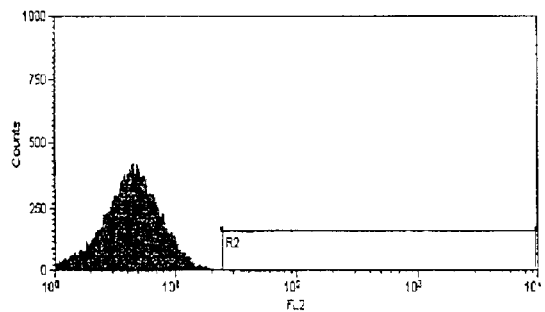
FIG. 4A shows a flow cytometry single parameter histogram of unstained RGC1 cells.
Figure 4B:
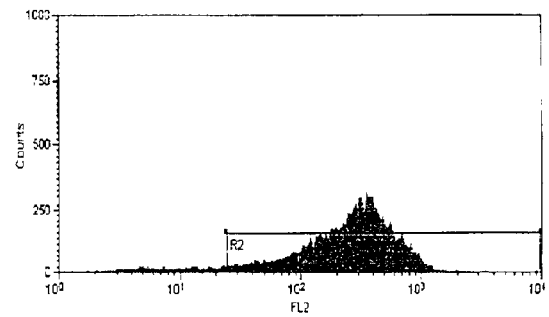
FIG. 4B shows a flow cytometry single parameter histogram of 4SC622 binding to FcγRI-expressing RGC1 cells as indicated by PE-AG184 binding.
Figure 4C:
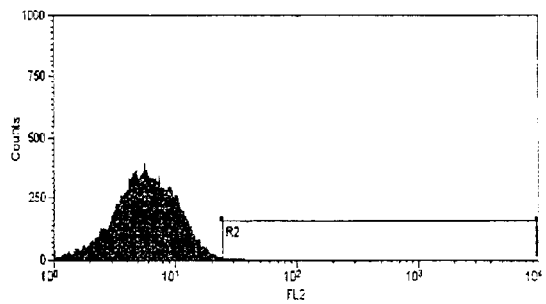
FIG. 4C shows a flow cytometry single parameter histogram of rat IgG blocking the binding of 4SC622 to RGC1 cells as indicated by loss of PE-AG184 binding.

Diffusion of Secreted Protein Between Expressing Cells and Non-expressing Cells Among Cells was Blocked by Adding IgG:

As all cells in a hFcγRI clonal cell line express a cell surface hFcγRI, they all possess the ability to bind IgG or fusion proteins consisting of the Fc domain of IgG. Because hFcγRI binds IgG from a variety of species (van de Winkel and Anderson, 1991), a panel of animal IgGs was tested for the ability to block the binding of a protein containing a human IgG1 (hIgG1) Fc tag (4SC622) to hFcγRI-expressing cells. 4SC622 is a chimeric molecule consisting of IL-2Rγ extracellular domain fused to the hIL-4Rγ extracellular domain which is then fused to the hIG-1Fc domain. In this experiment, cultures of RGC1, a hFcγRI-expressing cell line selected from CHO K1 cells that have been stably transfected with pTE084, were incubated with 1 µg/ml 4SC622 for 18 hours in the presence or absence of 1 mg/ml IgG from different species in a 37° C. tissue culture incubator. Cell surface binding of 4SC622 was determined by flow cytometry after washed cells were stained with phycoerythrin-conjugated mouse IgG1 monoclonal AG184 (PE-AG184) specific for the hIL-2Rγ component of 4SC622 (BD PharMingen; San Diego, Calif.), following procedures outlined for cell staining with FITC-hFc. FIG. 3 shows that hIgG completely blocked 4SC622 from binding to the hFcγRI expressed on the surface of RGC1. Rat, rabbit and canine-derived IgG also effectively blocked binding whereas bovine and ovine-derived IgG did not block. The ability of exogenously added rat IgG to block the binding of an exogenously added hIgG1 Fc-tagged protein (4SC622) to cell surface hFcγRI (FIG. 4) suggests that rat IgG can also block transfer between cells expressing a hIgG1 Fc-tagged protein at different levels. To test this, two cell lines that can be distinguished by the presence or absence of the green fluorescent protein (EGFP) were generated from RGC1. Briefly, to mark RGC1 cells with EGFP, $2 \times 10^6$ RGC1 cells were co-transfected with 0.5 µg PTE073 which encodes a hygromycin B phosphotransferase gene driven by phosphoglycerate kinase promoter, and 5 µg pRG816-EGFP which encodes EGFP gene driven by CMV-MIE promoter. The transfected cells were selected with 200 ug/ml hygromycin B (Sigma; St. Louis, Mo.) for two weeks. Green fluorescent cells were isolated by flow cytometry. One EGFP and hFcγRI-expressing clone, RGC2, was used in cell mixing experiments. The other cell line used in these experiments, RGC4, was generated by stable transfection of RGC1 with plasmid pEE14.1-622. pEE14.1-622 is a plasmid in which expression of 4SC622 is driven by the CMV-MIE promoter and includes a glutamine synthetase minigene, which confers resistance to the analog methionine sulfoximine (MSX), and allows for selection of stable integration events. RGC4 cells express hFcγRI on the cell surface and secrete the hIgG1 Fc-tagged protein 4SC622. One plate of mixed cells comprised of 50% RGC2 and 50% RGC4 cells was incubated with 1 mg/ml rat IgG for 18 hours prior to staining with PE-AG184 then examined by flow cytometry. FIG. 5A shows the EGFP flourescence of RGC2 cells and FIG. 5B shows that RGC2 cells also bind exogenously added 4SC622 (1 µg/ml) as indicated by an increase in PE-AG184 fluorescence. FIG. 5C shows that RGC4 did not fluoresce in the EGFP gate. Significantly, exogenously added rat IgG did not reduce the percentage of RGC4 cells that stained positive for cell surface 4SC622 (FIG. 5D) suggesting that the binding of 4SC622 to hFcγRI occurred while the proteins were in transit to the cell surface. When RGC2 and RGC4 cells were mixed (FIG. 5E), the 4SC622 protein secreted from RGC4 cells accumulated in the medium and bound most of the RGC2 cells. However, the addition of 1 mg/ml rat IgG significantly reduced the percentage of RGC2 cells that bound 4SC622 (FIG. 5F) demonstrating that rat IgG blocked the transfer of secreted hIgG1 Fc-tagged protein from expressing cells to non-expressing cells.

EXAMPLE 2

Figure 6:
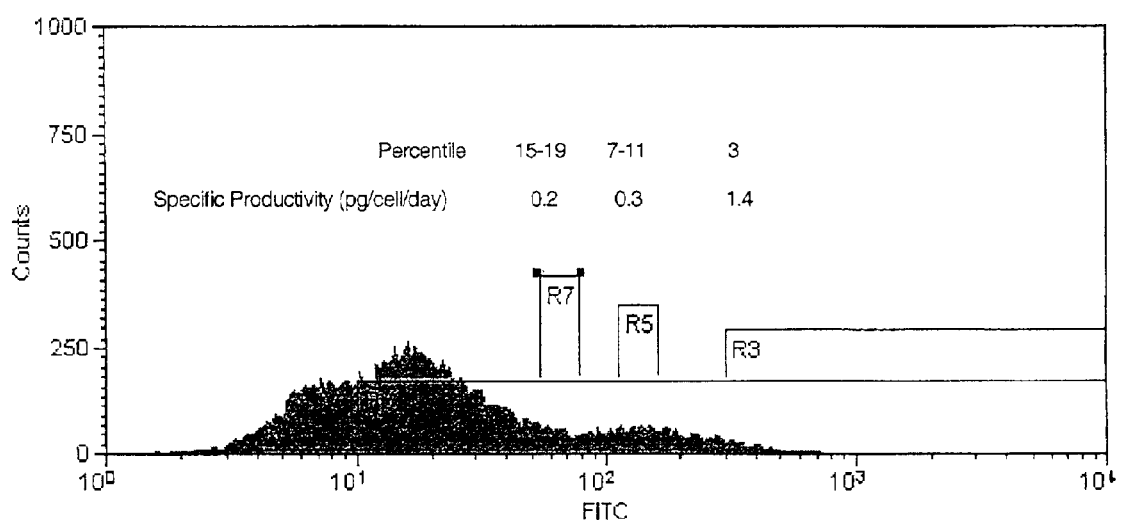
FIG. 6 shows a flow cytometry single parameter histogram of a MSX-resistant pool of RGC1 cells transfected with pEE14.1-622. Cells in the top 3% gate (R3), 7–11% gate (R5), and 15–19% gate (R7) were collected, expanded, and their 4SC622 productivity quantitated by immunostaining.

Cell Surface Fluorescence Correlates with the Expression Level of 4SC622:

RGC1 cells ($4 \times 10^6$) were transfected with pEE14.1-622 and a pool of stable transfectants was obtained after selection for 2 weeks in medium comprised of 10% dialyzed fetal bovine serum, 90% glutamine-free Dulbecco's modified eagle's medium, 1×GS supplement, and 25 uM MSX (All reagents were from JRH Biosciences, Lenexa, Kans.). Rat IgG was added to the culture medium to 1 mg/ml 18 hours prior to immunostaining. The cells were trypsinized, washed with PBS, and stained with 1.5 ug/ml of a polyclonal FITC-conjugated anti-human IgG (H+L) F(ab')$_2$fragment (Jackson ImmunoResearch Laboratories) for one hour at room temperature following procedures as described for FITC-hFc staining in Example 1. Cell staining was then analyzed by flow cytometry. The distribution of fluorescence suggested that the selected pool contained cells with a wide range of 4SC622 expression levels (FIG. 6). Cells in the top 3% (R3 bracket), 7–11% (R5 bracket), and 15–19% (R7 bracket) with respect to their immunofluorescence were sorted into three distinct pools and expanded for 9 days. Average 4SC622 production per cell for the pools was determined by measuring cell numbers and 4SC622 levels in the media after 3 days growth by an immuno-based Pandex assay (Idexx; Westbrook, Me.) following the manufacturer's recommendations. In the Pandex assay, fluoricon polystyrene assay particles coated with goat antihuman IgG, γ-chain specific antibody (Sigma) were used to capture 4SC622 from the medium, and a FITC-conjugated goat anti-human IgG, Fc specific (Sigma) was used to detect bead-bound 4SC622. Known amounts of purified 4SC622 were included in the assay for calibration. Cells in the top 3%, 7–11%, and 15–19% pool were found to produce 4SC622 at 1.42, 0.36, and 0.22 pg/cell/day, respectively. Thus, there was a correlation between cell surface 4SC622 staining and specific protein production. This result suggests that individual cells that express 4SC622 at high levels may be obtained by isolating cells that were stained brightest by the polyclonal FITC-conjugated anti-human IgG (H+L) F(ab')$_2$ fragment.

EXAMPLE 3

Isolation of Expression Clones in RGC1:

IL-4 Trap. To directly demonstrate the efficiency in generating clonal cell lines with high level secreted protein production by our methodology, clonal 4SC622 producing cell lines were generated from RGC1. RGC1 cells ($4 \times 10^6$) were transfected with pEE14.1-622, and selected for two weeks with 25 µM MSX to obtain a pool of stable transfectants. MSX-resistant cells were pooled and incubated with 1 mg/ml human IgG for 18 hours, prior to staining with PE-AG184. Six cells from the top 5% gate, as determined by flow cytometry analysis of cell surface 4SC622 staining, were isolated and expanded. 4SC622 production from the six clonal lines was determined and compared to 4SC622 production from clones obtained by hand-picking selected colonies followed by dilution cloning and amplification. One RGC1-derived clone, RGC4, produced 4SC622 at 12 pg/cell/day (FIG. 7). This level is similar to that of the best 4SC622 producer isolated by hand-picking and analyzing 2,700 clones. Thus, compared with hand-picking colonies, the methodology outlined in this invention proves to be far more efficient in the screening and cloning of high producers.

VEGF Trp. Plasmids pTE080 and pTE081 encode the genes for VEGF Traps, hVEGFR1R2 and hVEGF-R1R3. hVEGF-R1R2 is a chimeric molecule consisting of the first Ig domain of hVEGFR1 fused to the second Ig domain of hVEGFR2 which is then fused to the hIg1FC domain. hVEGFR1R3 is a chimeric molecule consisting of the first Ig domain of hVEGFR1 fused to the second Ig domain of hVEGFR3 which is then fused to the hIg1FC domain. In these plasmids, the gene for the VEGF Trap is driven by the CMV-MIE promoter and a glutamine synthetase minigene, which confers resistance to MSX, is expressed for selection of stable integration events. RGC1 cells were transfected with either of these plasmids and grown in medium containing 25 µM MSX for 2 weeks to select for cells in which the plasmid has stably integrated. MSX-resistant cells were incubated with 0.1 ug/ml Ig2a and mouse IgG3 for 18 hours prior to staining with 1.5 ug/ml polyclonal FITC-conjugated anti-human IgG (H+L) F(ab')$_2$fragment. Cell were stained for 1 hour then washed twice with PBS prior to flow cytometry. Single cells were sorted into 96-well tissue culture plates from the pool of cells whose fluorescence was among the highest 1%. The cells in individual wells were expanded and their productivities were determined by Pandex assays. FIG. 7 shows that RGC-derived clones expressing both hVEGFR1R2 and hVEGFR1R3 had higher specific productivities and were isolated by screening fewer clones as compared to the highest-expressing hand-picked MSX-resistant colonies.

EXAMPLE 4

Figure 9:
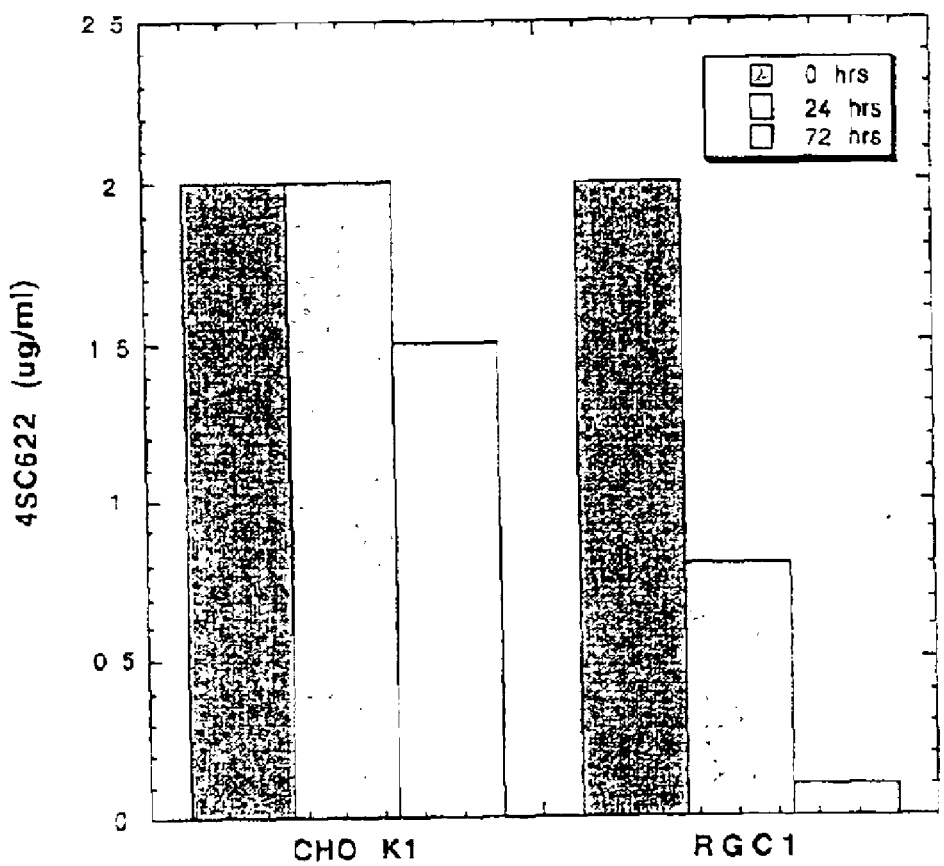
FIG. 9 shows that expression of the gene for hFcγRI results in loss of 4SC622 from the culture medium. RGC1 cells, or CHO K1 parental cells, were incubated in medium containing 2 ug/ml 4SC622. The concentration of 4SC622 remaining in the media was quantitated by immuno-staining after 24 hours, and 72 hours incubation.

Cell Surface-bound hIgG1 Fc-tagged Protein is Internalized by RGC1:

hFcγRI is known to induce internalization of its cell surface-bound ligand. To analyze whether RGC1 cells could internalize cell surface-bound 4SC622, 1 ug/ml 4SC622 was added to RGC1 cells for 1 hour and then the cells were immediately processed for 4SC622 immunostaining with PE-AG184 and flow cytometry analysis. 93% of the cells stained positive for cell surface 4SC622 (FIG. 8B). Alternatively, 1 ug/ml 4SC622 was added to RGC1 cells for 1 hour, then the cells were washed and incubated in culture medium without 4SC622 with PE-AG184 for 18 hours. Flow cytometry analysis following immunostaining for 4SC622 showed that 9% of the cells retained 4SC622 on the cell surface (FIG. 8C). To further characterize the loss of surface-bound 4SC622, purified 4SC622 protein was added to the media of RGC1 and parental CHO K1 cells, then levels of 4SC622 in the media were measured over time. FIG. 9 shows that 4SC622, added to 2 μg/ml to the culture media in a 10 cm plate, was significantly lower in RGC1 conditioned medium after 3 days incubation as compared to the CHO K1 control. These results show that the concentration of 4SC622 in the culture medium is reduced by the presence of hFcγRI on the cell surface. The results suggest that the depletion of 4SC622 from the media was the result of hFcγRI-4SC622 complex internalization. This internalization of receptor-ligand complexes may facilitate the effective removal of all 4SC622 from non-expressing cells in the presence of blocking IgG during the 18 hour blocking step.

Figure 10:
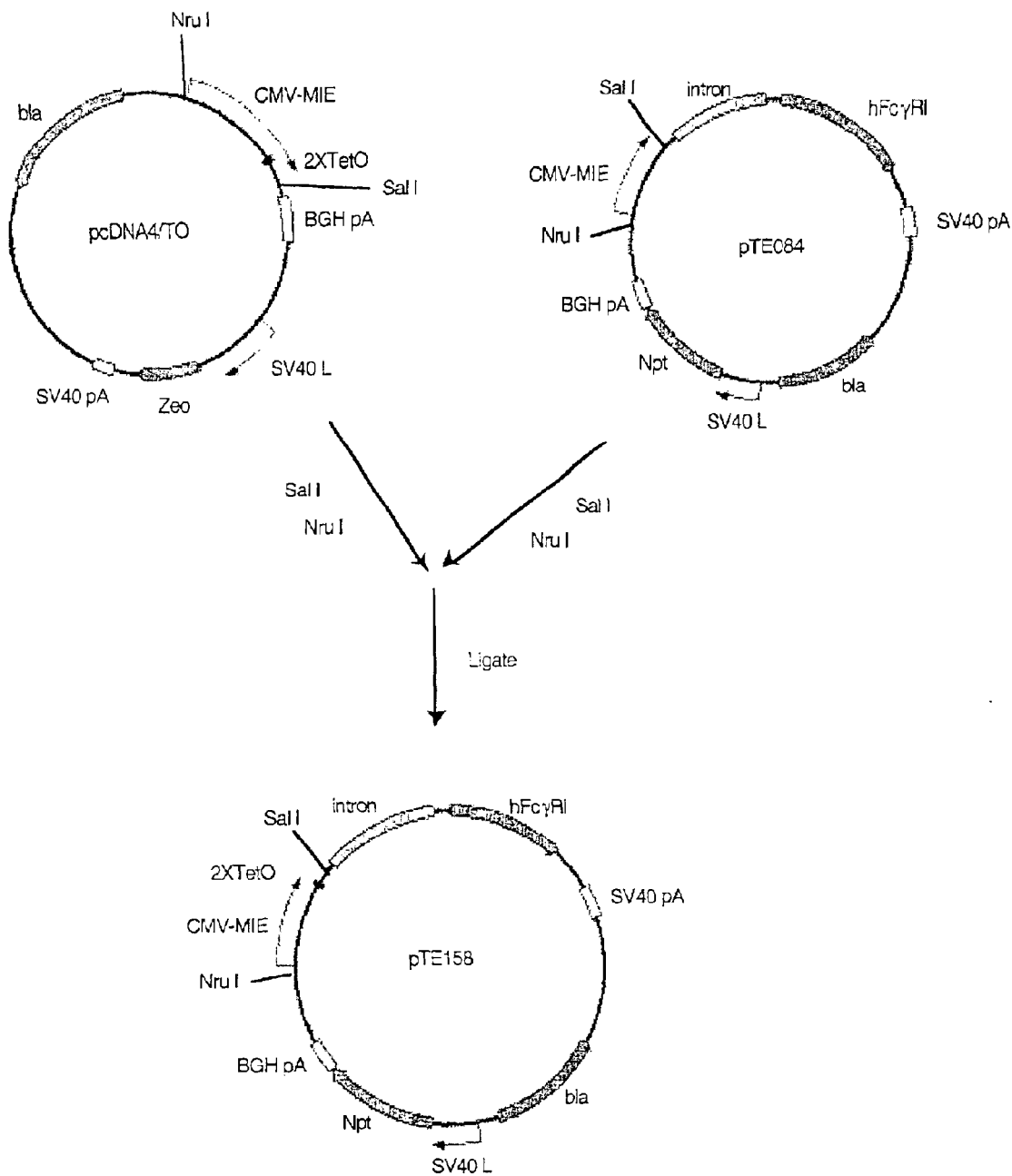
FIG. 10 represents the construction of pTE158, designed to allow TetR-regulated expression of human FcγRI. Two repeats of the tet operator sequence (TetO) are immediately downstream of the CMV promoter in pTE158.

EXAMPLE 5
Construction of CHO K1 Cell Lines with Inducible hFcγRI Expression:

Flow cytometry-based autologous secretion trap methods that utilize the hFcγRI allow rapid isolation of high expression clones. However, if hFcγRI mediates turnover of Fc-tagged proteins, then the realized production of the secreted protein by engineered hFcγRI expressing cells would be higher if hFcγRI expression could be inhibited during the production period. To this end, a CHO K1 cell line in which the expression of hFcγRI is induced by tetracycline, or the analog doxycycline, was constructed. In this system, CHO K1 cells were first engineered to express the tetracycline repressor protein (TetR) and hFcγRI was placed under transcriptional control of a promoter whose activity was regulated by TetR. Two tandem TetR operators (TetO) were placed immediately downstream of the CMV-MIE promoter/enhancer in pTE084 to generate pTE158 (FIG. 10). Transcription of hFcγRI from the CMV-MIE promoter in pTE158 was blocked by TetR in the absence of tetracycline or some other suitable inducer. In the presence of inducer TetR protein was incapable of binding TetO and transcription of hFcγRI occurs.

CHO K1 cells were transfected with pcDNA6/TR, a plasmid that confers resistance to blasticidin in which expression of TetR originates from the CMV-MIE promoter (Invitrogen; Carlsbad, Calif.) After two weeks of selection with 2.5 ug/ml blasticidin (Invitrogen), the stable transfectants were pooled. This pool was then transfected with pTE158, a plasmid that confers resistance to G418 in which the expression of hFcγRI is dependent on a CMV-MIE/TetO hybrid promoter. The cells consecutively transfected with pcDNA6/TR and pTE158 were selected with 400 ug/ml G418 and 2.5 ug/ml blasticidin for 12 days then pooled. The pool was induced for two days by the addition of 1 μg/ml doxycycline then stained with FITC-hFc to identify cells that express hFcγRI. The top 5% of cells expressing hFcγRI were collected as a pool, expanded for 6 days in the absence of doxycycline, and were again stained with FITC-hFc for the presence of hFcγRI. Cells that did not stain for hFcγRI were collected and expanded in culture medium containing 1 μg/ml of doxycycline for three days. The pool was then stained for the presence of hFcγRI and were isolated by flow cytometry. Cells that expressed the highest levels of hFcγRI (top 1%) were sorted onto 96 well plates at one cell per well. These cells presumably contained cell that had low non-induced expression levels of FcR1 and high inducible levels of FcR1. After expansion, the induction of hFcγRI by doxycycline in 20 clones was confirmed by immunostaining with FITC-hFc and flow cytometry. One clone was chosen for further characterization and was named RGC10. FIG. 11 shows that in the absence of doxycycline RGC10 did not express detectable levels of hFcγRI, whereas high levels of hFcγRI were observed in cells that were induced with 1 μg/ml of doxycycline for three days. The mean fluorescence of RGC10 cells increased by more than 1,000 fold after induction by doxycycline.

EXAMPLE 6
Isolation of 4SC622-producing Cell Lines from RGC10:

RGC10 cells were transfected with pEE14.1-622, and MSX-resistant cells were pooled after selection with 25 μM MSX for two weeks. Expression of hFcγRI was induced by the addition of 1 μg/ml of doxycycline to the culture medium for three days. One mg/ml rat IgG was added to the culture medium containing doxycycline 18 hours prior to staining with polyclonal FITC-conjugated anti-human IgG (H+L) F(ab')$_2$ fragment and analysis by flow cytometry. Cells that expressed the highest levels of 4SC622 (top 1%) were sorted into 96 well plates at 1 cell per well (FIG. 12C). FIG. 12B shows that without induction of hFcγRI expression by doxycycline, staining with polyclonal FITC-conjugated anti-human IgG (H+L) F(ab')$_2$ fragment fails to detect cell surface bound 4SC622. Sixty clones were expanded in the absence of doxycycline. FIG. 13 shows the specific productivity of the 13 highest producers as determined by Pandex assay. The specific productivity of clone 1C2 was 17.8 pg/cell/day, significantly better than the 12 pg/cell/day observed for the best 4SC622 cell line previously isolated using the unregulated hFcγRI cell line RGC1.

Figure 14:
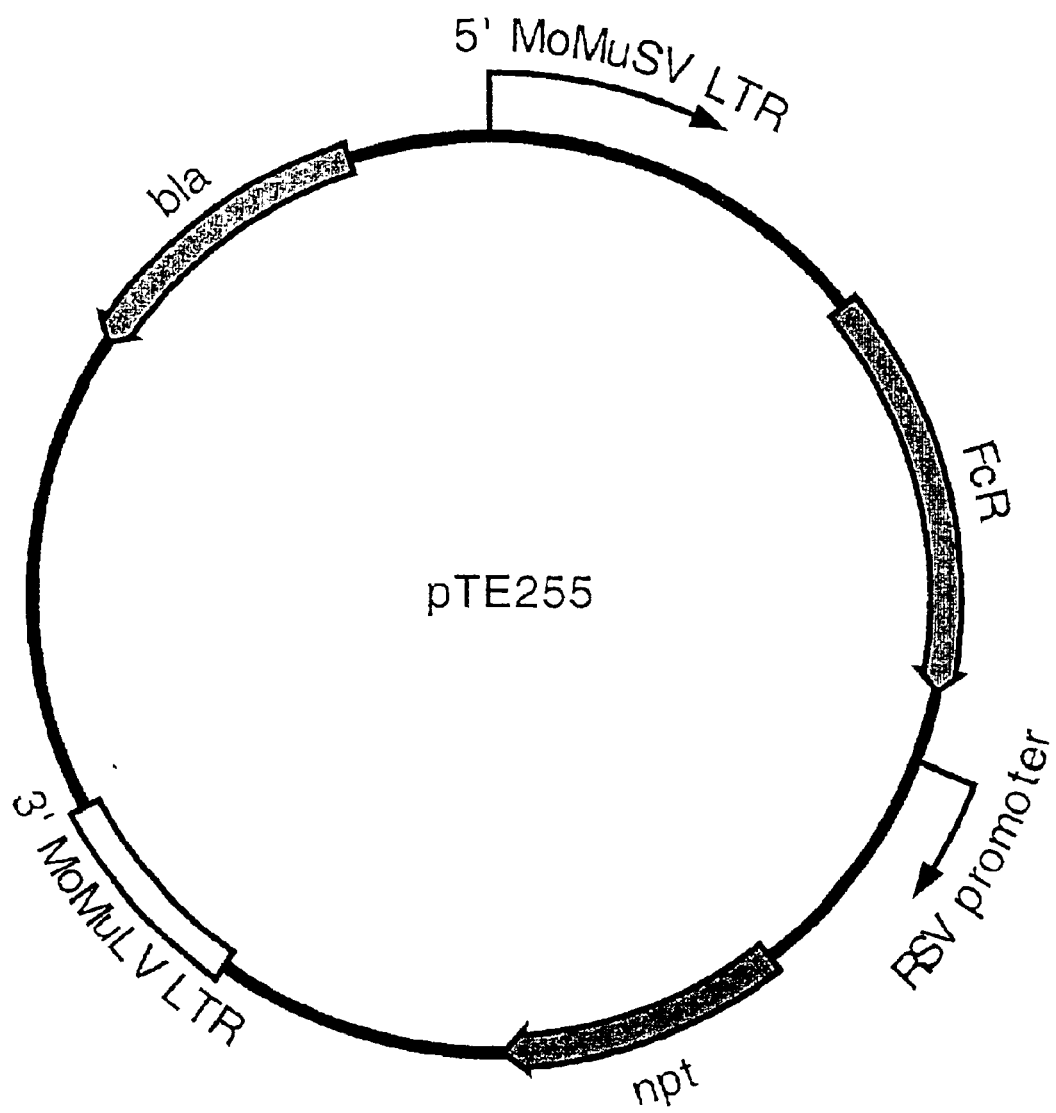
FIG. 14 represents the structure of pTE255, designed for the constitutive expression of human FcγRI from the upstream MoMuSV LTR promoter.
Figure 15A:
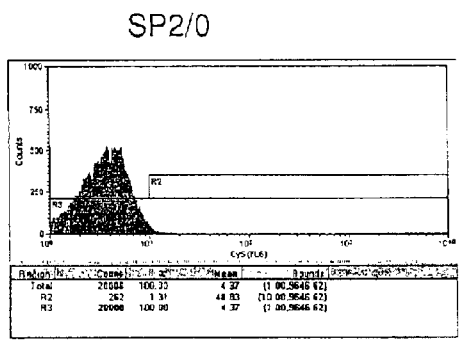
FIG. 15A shows a flow cytometry single parameter histogram of unstained Sp2/0 cells.
Figure 15B:
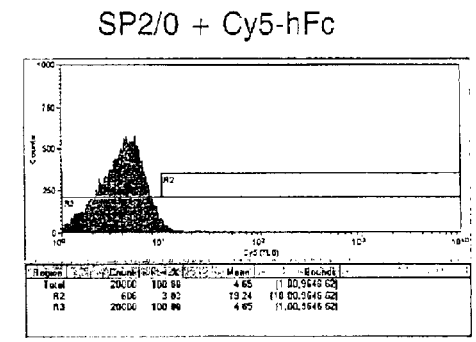
FIG. 15B shows a flow cytometry single parameter histogram of Cy5-hFc stained Sp2/0 cells.
Figure 15C:
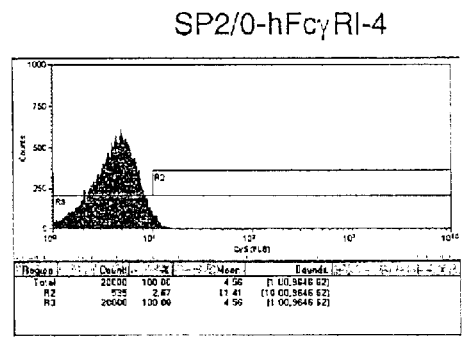
FIG. 15C shows a flow cytometry single parameter histogram of unstained Sp2/0-FcR-4 cells.
Figure 15D:
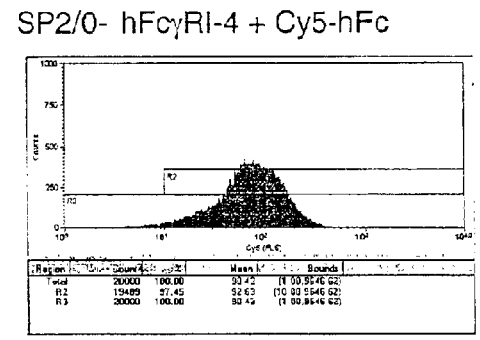
FIG. 15D shows a flow cytometry single parameter histogram of Cy5-hFc stained Sp2/0-FcR-4 cells.

EXAMPLE 7
Sp2/0 Myeloma Cells can be Engineered to Express a Cell Surface Capture Protein:

In this example, the Sp2/0-Ag14 myeloma cell line was engineered to stably express hFcγRI to demonstrate that the autologous secretion trap method was applicable to cell lines other than CHO. The gene for hFcγRI was introduced into the myeloma cell by retroviral infection. The plasmid pLXRN (Clontech; Palo Alto, Calif.), a retroviral DNA vector wherein a gene of interest may be expressed from the upstream Moloney murine sarcoma virus long terminal repeat (MoMuSV LTR) promoter, was used to generate retrovirus encoding the hFcγRI gene. The 1,363 bp Xho I fragment from pTE084, encoding the human FcγRI gene, was cloned into the Xho I site of pLXRN. A plasmid in which hFcγRI cDNA expression was dependent on the MoMuSV LTR was chosen and named pTE255 (FIG. 14).

Pantropic retrovirus for the expression of hFcγRI was generated essentially following the manufacturer's guidelines. The packaging cell line GP-293, a HEK 293-based cell line that stably expresses the viral gag and pol proteins (Clontech; Palo Alto, Calif.), was co-transfected with 10 μg each of pVSV-G and pTE255. The plasmid pVSV-G allows expression of the viral envelope protein VSV-G that confers broad host range upon the infective particles.

Construction of Sp2-hFcγRI-4:

The pantropic hFcγRI retrovirus was used to infect 1×10$^7$ Sp2/0-Ag14 myeloma cells (American Type Culture Collection; Manassas, Va.) at a multiplicity of about 10 infective particles per cell. Three days after infection, cells were stained for 1 hour then washed twice with PBS prior to analysis by flow cytometry. Those cells expressing hFcγRI, as indicated by bound FITC-hFc, were collected as a pool by flow cytometry. The pool was expanded for 13 days then again stained with FITC-hFc and cells expressing hFcγRI were collected as a pool by flow cytometry. These sorted cells were cultured in 10% fetal bovine serum 90% Dulbecco's Modified Eagle's Medium (D-MEM) with 4.5 g/l glucose and 4 mM glutamine for 3 weeks, stained with FITC-hFc, and the cells with mean fluorescence in the top 1% of the population were cloned by single cell sorting. After expansion, 24 clones were examined by flow cytometry for expression of hFcγRI, as described above, and one clone, Sp2-hFcγRI-4, was chosen for additional characterization (FIG. 15).

Figure 16:
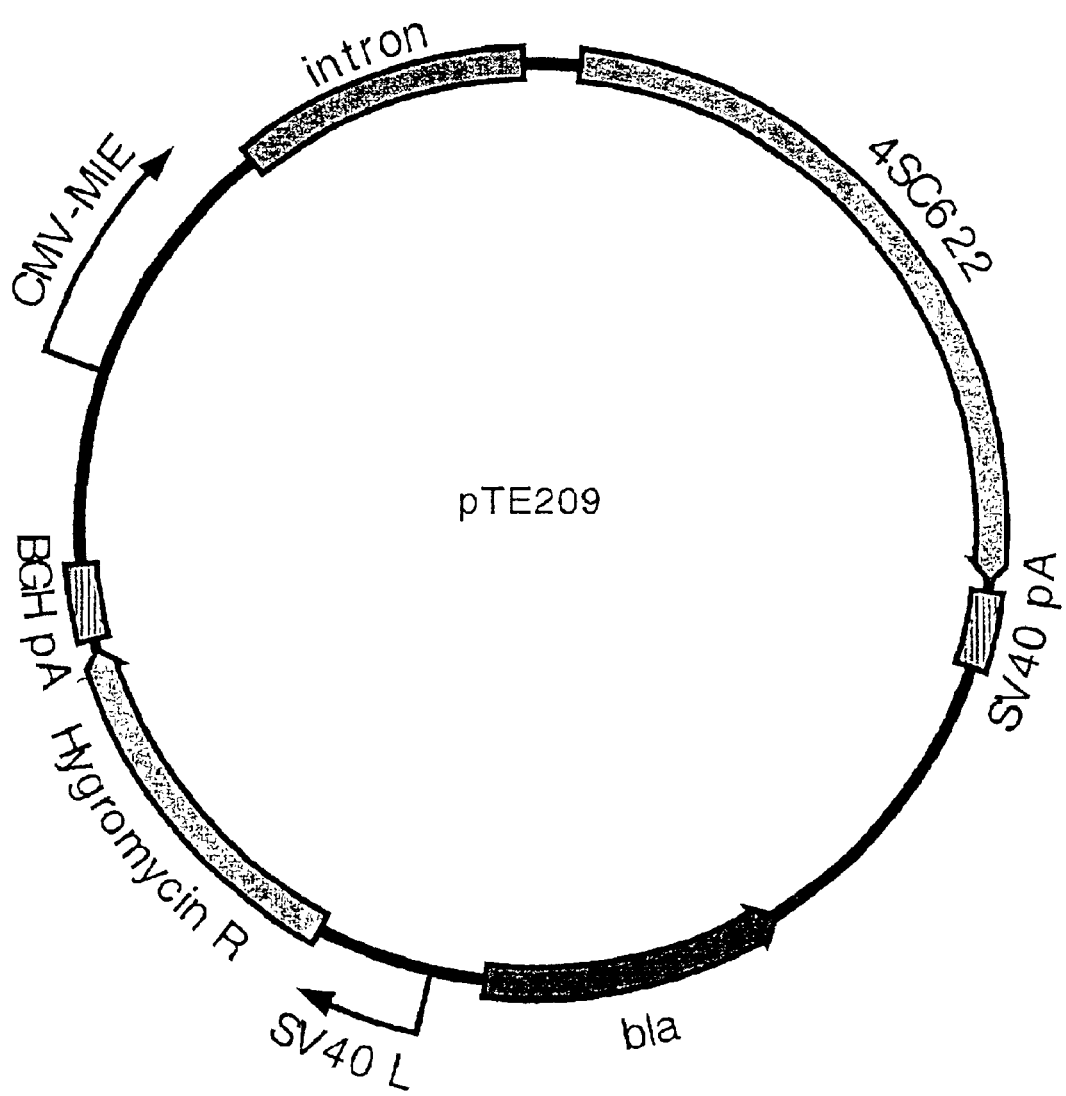
FIG. 16 represents the structure of pTE209, designed for the constitutive expression of 4SC622 from the upstream CMV MIE promoter.
Figure 17A:
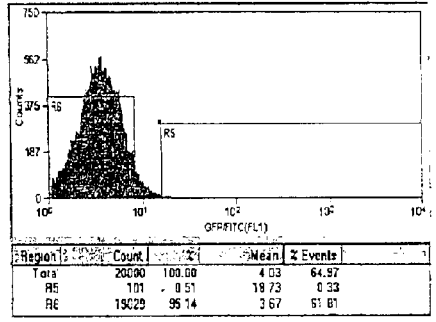
FIG. 17A shows a flow cytometry single parameter histogram of unstained hygromycin B-resistant Sp2/0-FcR-4 cells transfected with pTE209.
Figure 17B:
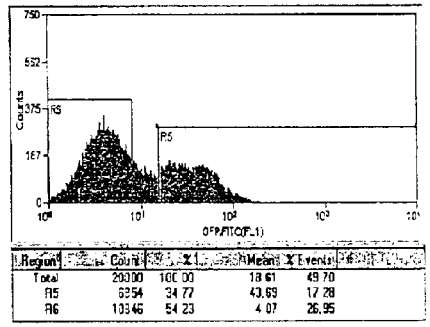
FIG. 17B shows a flow cytometry single parameter histogram of hygromycin B-resistant Sp2/0-FcR-4 cells transfected with pTE209 and incubated with rabbit IgG (1 mg/ml) for 18 hours prior to staining with polyclonal FITC-conjugated anti-human IgG (H+L) F(ab')$_2$ fragment.
Figure 17C:
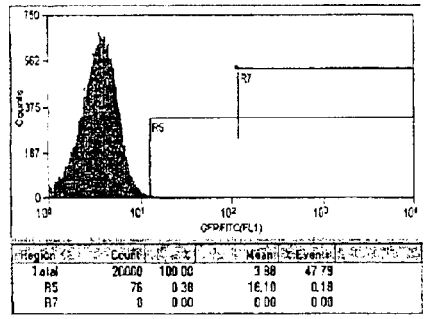
FIG. 17C shows a flow cytometry single parameter histogram of unstained cells expanded from the top 1% most fluorescent cells in FIG. 4B.
Figure 17D:
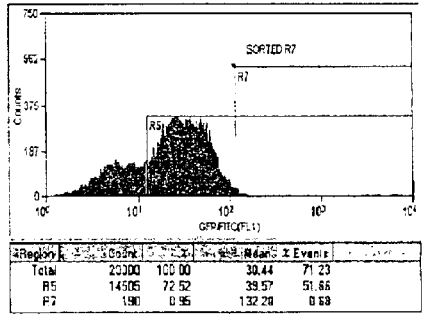
FIG. 17D shows a flow cytometry single parameter histogram of the cells expanded from the top 1% most fluorescent cells in FIG. 4B, incubated with rabbit IgG (1 mg/ml) for 18 hours prior to staining with polyclonal FITC-conjugated anti-human IgG (H+L) F(ab')$_2$ fragment.
Figure 17E:
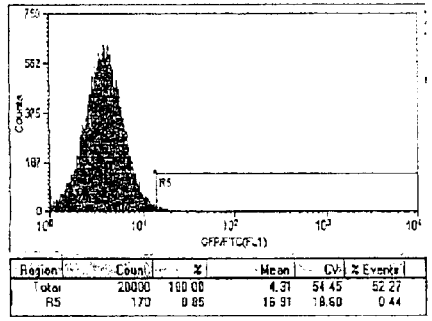
FIG. 17E shows a flow cytometry single parameter histogram of unstained clone 5H11 cells.
Figure 17F:
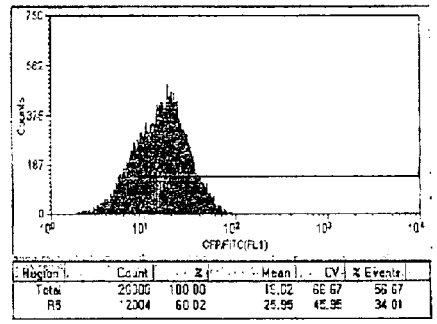
FIG. 17F shows a flow cytometry single parameter histogram of clone 5H11 cells incubated with rabbit IgG (1 mg/ml) for 18 hours prior to staining with polyclonal FITC-conjugated anti-human IgG (H+L) F(ab')$_2$ fragment.

Isolation of Sp2-hFcγRI-4 Cells Expressing 4SC622 Protein:

Sp2-hFcγRI-4 cells (1×10$^7$)were transfected with pTE209 (FIG. 16), a plasmid that allows constitutive expression of 4SC622 from the CMV-MIE promoter and confers resistance to hygromycin. The transfected cells were placed in medium containing 10% FCS, 90% D-MEM and 400 μg/ml hygromycin for 14 days. Hygromycin-resistant cells were incubated with 1 mg/ml rabbit IgG for eighteen hours prior to staining with polyclonal FITC-conjugated anti-human IgG (H+L) F (ab')$_2$fragment. Cells were stained for 1 hour then washed twice with PBS prior to analysis by flow cytometry. Labeled cells were collected as a pool by flow cytometry then cultured for 5 days and sorted as described above. Cells from the expanded pool that bound the most polyclonal FITC-conjugated anti-human IgG (H+L) F (ab')$_2$fragment, top 1% population, were then cloned by single cell sorting (FIG. 17). Production of 4SC622 from ten clones was analyzed by ELISA and all 10 clones were found to express 4SC622; clone 5H11 produced 4SC622 at 0.5 pg per cell per day. These data showed that clones secreting 4SC622 were efficiently isolated by the autologous secretion trap method from a heterogeneous pool of cells derived from stable transfection of Sp2-hFcγRI-4 cells with pTE209.

To confirm that 4SC622 was autologously displayed on the surface of myeloma cells expressing both 4SC622 and hFcγRI, clone 5H11 was incubated with 1 mg/ml rabbit IgG for 18 hours then stained with FITC-conjugated anti-human IgG (H+L) F(ab')$_2$fragment and found to display cell surface 4SC622. Secreted protein was displayed under conditions in which cross-feeding was blocked by rabbit IgG, demonstrating the autologous display of 4SC622. These data indicated that the autologous secretion trap method described above was not limited to CHO cells and may be extended to myeloma and other cell types as well.

EXAMPLE 8

Figure 18:
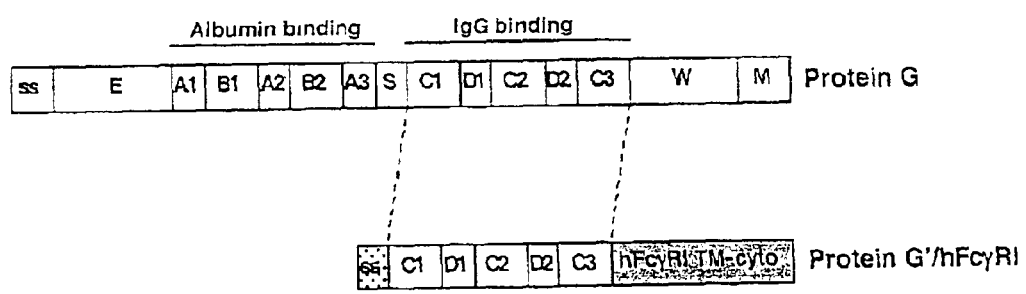
FIG. 18 shows schematic diagrams of domains of Protein G and Protein G/hFcγRI fusion protein encoded in pTE300.
Figure 19:
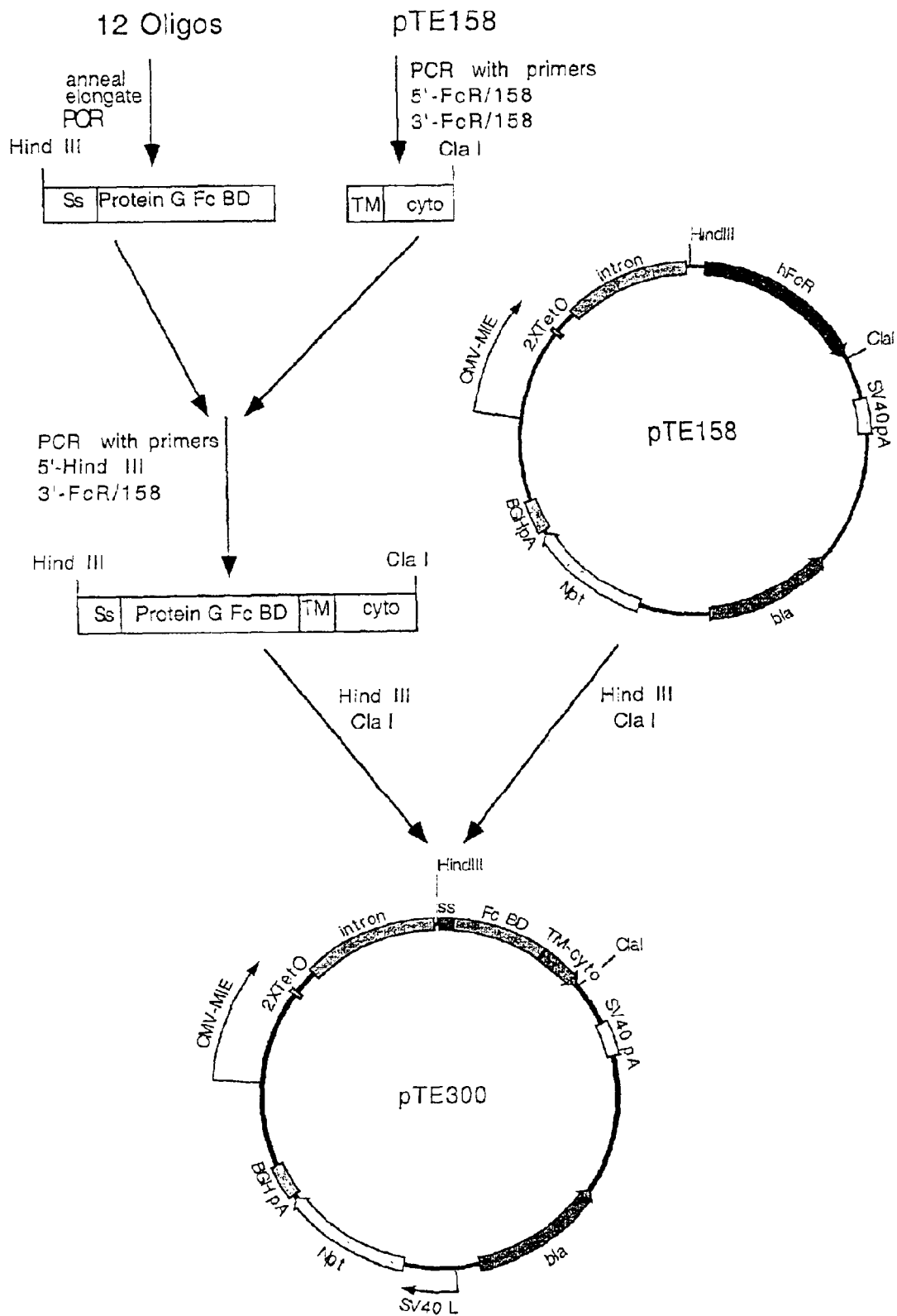
FIG. 19 is an outline of the construction of pTE300, designed for the expression of a chimeric protein containing the RORI signal sequence, the Fc binding domain of Protein G, and the transmembrane and intracellular domain of hFcγRI from the upstream CMV MIE promoter.
Figure 20A:
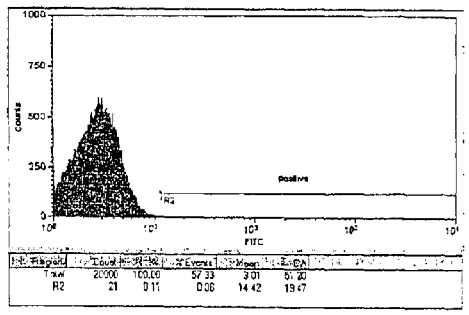
FIG. 20A shows a flow cytometry single parameter histogram of unstained RGC14 cells.
Figure 20B:
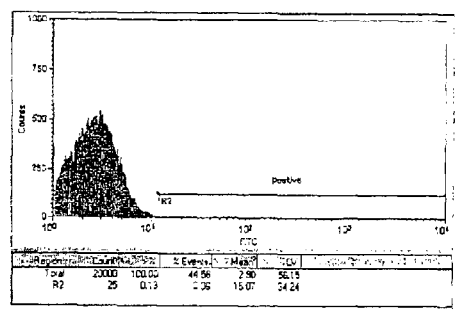
FIG. 20B shows a flow cytometry single parameter histogram of FITC-hFc stained RGC14 cells.
Figure 20C:
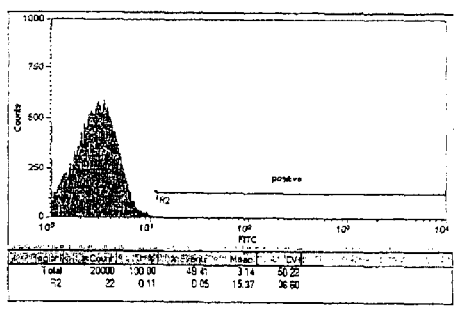
FIG. 20C shows a flow cytometry single parameter histogram of unstained G418-resistant RGC14 cell pool transfected with pTE300.
Figure 20D:
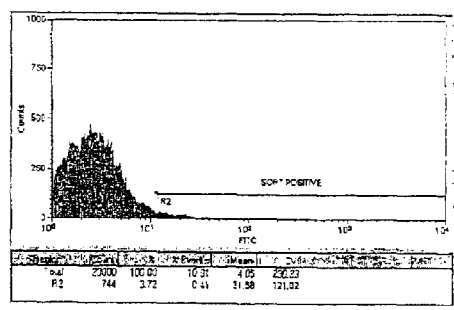
FIG. 20D shows a flow cytometry single parameter histogram of FITC-hFc stained G418-resistant RGC14 cell pool transfected with pTE300.
Figure 20E:
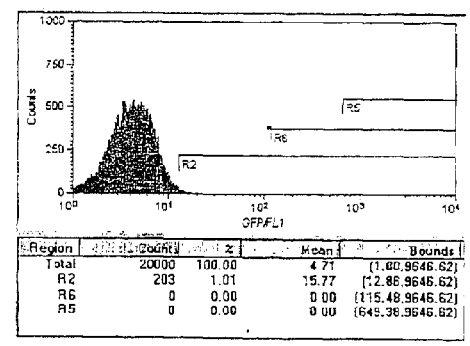
FIG. 20E shows a flow cytometry single parameter histogram of unstained RGC18 cells.
Figure 20F:
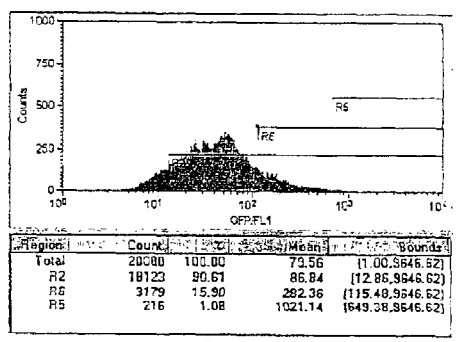
FIG. 20F shows a flow cytometry single parameter histogram of RGC18 cells incubated with 10% fetal bovine serum for 2 hours prior to staining with polyclonal FITC-conjugated anti-bovine IgG (H+L) F(ab')$_2$ fragment.

A Protein G Chimeric Protein Can Function as a Cell Surface Capture Protein:

To demonstrate the application of the autologous secretion trap method to a cell surface capture protein other than hFcγRI, a cell line expressing Protein G was constructed. Protein G, from the *Streptococcus* strain G148, binds to all human and mouse IgG subclasses, and as such has utility for the isolation of recombinant cells expressing antibodies or IgG Fc fusion proteins. To demonstrate that the Protein G IgG Fc binding domain could be used as a cell surface capture protein capable of binding to all human and mouse IgG subclasses, we constructed a CHO line expressing a chimeric protein comprised of the Fc binding domain of Protein G fused to the hFcγRI transmembrane and intracellular domain (FIG. 18 ). The Fc binding domain of Protein G contains three homologous repeats of 55 amino acids long (Guss et al., (1986) EMBO 5:1567 and Sjobring et al., (1991) J. Biol. Chem. 266:399) and each repeat is capable of binding one IgG Fc. To improve the expression of this chimeric protein in CHO cells, we constructed a synthetic DNA in which the signal sequence from the mouse ROR1 gene was fused to the Fc binding domain, amino acids 303 to 497 (SEQ ID NO:1), of Protein G (accession #X06173). This synthetic DNA was generated by a combination of oligonucleotide annealing, gap filling, and PCR amplification. The synthetic DNA was then fused, by PCR, to DNA encoding the transmembrane and intracellular domains, amino acids 279 to 374 (SEQ ID NO:2), of hFcγRI (accession M21091). The resultant DNA encoding the Protein G/hFcγRI chimeric protein was cloned into pTE158 downstream of the CMV-MIE promoter, replacing the gene encoding hFcγRI, to yield the plasmid pTE300 (FIG. 19 ).

A CHO K1 cell line adapted to grow in serum-free medium, RGC14, was transfected with pTE300, and after three days 400 μg/ml G418 was added to the culture medium to select for stable integration of pTE300. Two weeks after the start of selection, the cells were stained with FITC-hFc to identify cells that expressed hFcγRI. These cells were analyzed by flow cytometry and cells expressing hFcγRI were collected as a pool (FIG. 20). The cells were expanded for 10 days and the population of cells expressing hFcγRI was again isolated by flow cytometry. The cells were again expanded, stained with FITC-hFc, and single cells expressing high levels of the Protein G/hFcγRI chimeric protein were isolated by flow cytometry. Single cells that stained positive for FITC-hFc binding were sorted into medium composed of 10% fetal bovine serum, 90% Ham's F12, and 400 μg/ml G418. After two weeks incubation, 48 clones were examined for binding to bovine IgG present in the culture medium by staining with FITC-conjugated anti-bovine IgG F(ab')$_2$ fragment (Jackson ImmunoResearch Laboratories, West Grove, Pa.). One clone, RGC18 that stained positive with this antibody was chosen for further characterization.

Figure 21A:
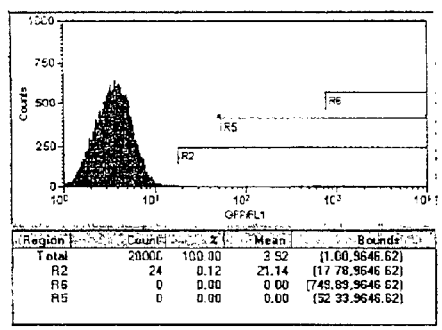
FIG. 21A shows a flow cytometry single parameter histogram of unstained hygromycin B-resistant cell pool derived from RGC18 after transfection with pTE209.
Figure 21B:
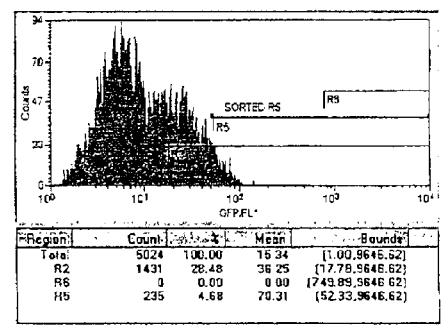
FIG. 21B shows a flow cytometry single parameter histogram of the hygromycin B-resistant cell pool derived from RGC18 after transfection with pTE209, incubated with rabbit IgG (1 mg/ml) for 18 hours prior to staining with polyclonal FITC-conjugated anti-human IgG (H+L) F(ab')$_2$ fragment.
Figure 22A:
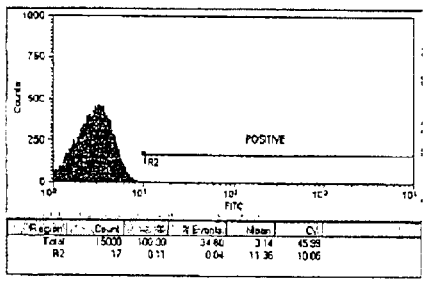
FIG. 22A shows a flow cytometry single parameter histogram of unstained RGC18 cells.
Figure 22B:
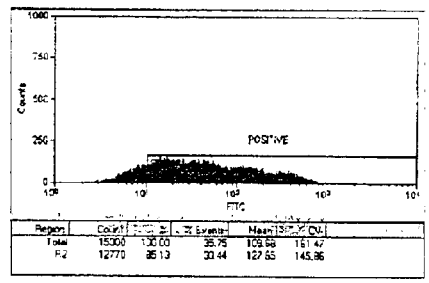
FIG. 22B shows a flow cytometry single parameter histogram of RGC18 cells incubated with 4SC622 (1 μg/ml) for 1 hour prior to staining with polyclonal FITC-conjugated anti-human IgG (H+L) F(ab')$_2$ fragment.
Figure 22C:
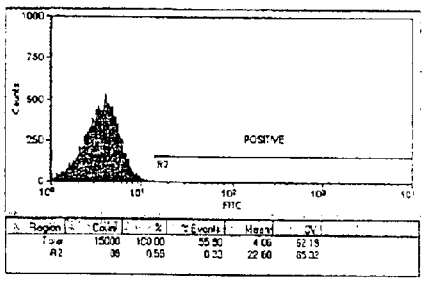
FIG. 22C shows a flow cytometry single parameter histogram of RGC18 cells incubated with 4SC622 (1 μg/ml) and rabbit IgG (1 mg/ml) for 1 hour prior to staining with polyclonal FITC-conjugated anti-human IgG (H+L) F(ab')$_2$ fragment.
Figure 22D:
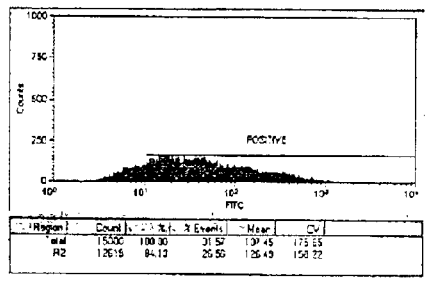
FIG. 22D shows a flow cytometry single parameter histogram of RGC18 cells incubated with 4SC622 (1 μg/ml) for 18 hours prior to staining with polyclonal FITC-conjugated anti-human IgG (H+L) F(ab')$_2$ fragment.
Figure 22E:
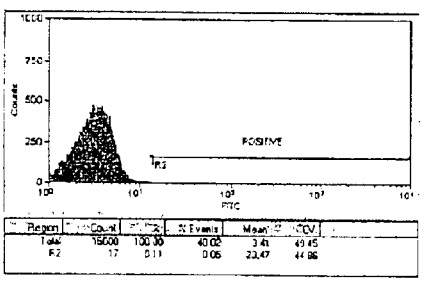
FIG. 22E shows a flow cytometry single parameter histogram of RGC18 cells incubated with 4SC622 (1 μg/ml) for 2 hours then with 4SC622 (1 μg/ml) and rabbit IgG (1 mg/ml) for 18 hours prior to staining with polyclonal FITC-conjugated anti-human IgG (H+L) F(ab')$_2$ fragment.
Figure 22F:
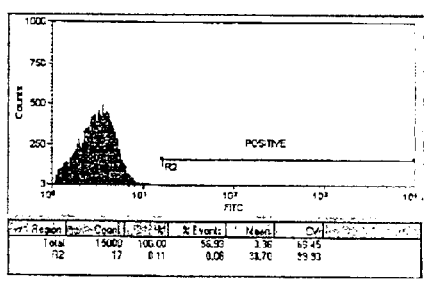
FIG. 22F shows a flow cytometry single parameter histogram of unstained RGC19 cells derived from RGC18 cells by transfection with pTE209.
Figure 22G:
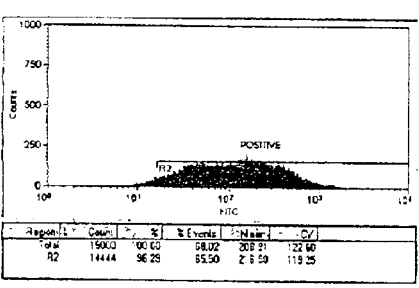
FIG. 22G shows a flow cytometry single parameter histogram of RGC19 cells stained with polyclonal FITC-conjugated anti-human IgG (H+L) F(ab')$_2$ fragment.
Figure 22H:
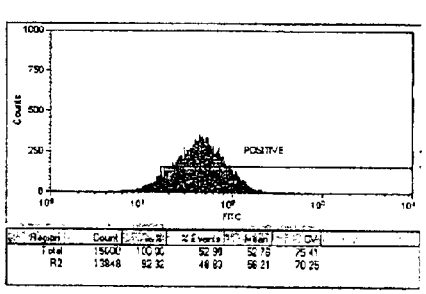
FIG. 22H shows a flow cytometry single parameter histogram of RGC19 cells incubated with rabbit IgG (1 mg/ml) for 18 hours prior to staining with polyclonal FITC-conjugated anti-human IgG (H+L) F(ab')$_2$ fragment.

Isolation of Expression Clones in RGC18:

RGC18 cells (6×10$^6$) were transfected with pTE209 and selected for integration of the plasmid by growth in 400 μg/ml hygromycin for 18 days. Hygromycin-resistant cells were incubated with 1 mg/ml rabbit IgG for eighteen hours prior to staining with polyclonal FITC-conjugated anti-human IgG (H+L) F (ab')$_2$fragment. Cells were stained for 1 hour then washed twice with PBS prior to analysis by flow cytometry (FIG. 21). The most fluorescent cells (top 5%) were isolated by single cell sorting and expanded for 3 weeks. Ten clones were examined for 4SC622 secretion. All clones tested secreted 4SC622 at high level, and the best clone, RGC19, had a specific productivity of 6.4 pg/cell day. This result demonstrated that 4SC622-expressing cells were efficiently isolated from a heterogeneous pool of cells derived from stable transfection of RGC18 with pTE209 by the autologous secretion trap method. Furthermore, these data clearly demonstrated that a fragment of Protein G could be engineered to include a signal sequence and transmembrane domain, and function as a cell surface capture protein.

To confirm that 4SC622 was autologously displayed on the surface of RGC19 cells expressing both Protein G/hFcγRI chimeric protein and 4SC622, RGC19 was incubated with 1 mg/ml rabbit IgG for 18 hours then stained with FITC-conjugated anti-human IgG (H+L) F(ab')$_2$fragment and analyzed by flow cytometry. RGC19 cells were found to possess cell surface 4SC622 under these conditions in which cross-feeding was blocked by rabbit IgG, suggesting autologous display of 4SC622 (FIG. 22). Rabbit IgG effectively blocked binding of exogenous 4SC622 protein to RGC18 cells, but did not block display of 4SC622 on the cell surface of cells expressing 4SC622. These data demonstrated that the properties of the Protein G/hFcγRI chimeric protein were similar to those of hFcγRI as a cell surface capture protein, and suggested that the autologous secretion trap method can employ other proteins as cell surface capture proteins.

EXAMPLE 9

Isolation of Antibody-producing Cells from RGC10:

To demonstrate the utility of the autologous secretion trap method for the isolation of CHO cell lines that express recombinant antibodies we cloned the DNA encoding variable light and variable heavy genes from the KD5 hybridoma. KD5 is a hybridoma that expresses a monoclonal antibody specific for the human Tie-2 receptor.

The mouse IgG constant region gene sequences were cloned from 500 ng of mouse spleen polyA+ RNA (Clontech, Palo Alto, Calif.). Single stranded cDNA was synthesized using SuperScript First-Strand Synthesis System for RT-PCR, primed with 50 ng of random hexamers (Invitrogen Life Technologies, Carlsbad, Calif.). The mouse kappa light constant DNA sequence (accession #Z37499) was amplified from this cDNA by PCR using the primers 5' mCLK1 (Z37499) (5'-CGGGCTGATGCTGCACCAACTGTATCCATCTTC-3') (SEQ ID NO:3) and 3' mCLK1(Z37499) (5'-ACACTCTCCCCTGTTGAAGCTCTTGACAATGGG-3') (SEQ ID NO:4). The mouse IgG2a constant region DNA sequence (accession #AJ294738) was also amplified from this cDNA by PCR using the primers 5' mCH2a(AJ294738) (5'-GCCAAAACAACAGCCC,CATCGGTCTATCCAC-3') (SEQ ID NO:5) and 3' mCH2a(AJ294738) (5'-TCATTTACCCGGAGTCCGGGAGAAGCTCTTAGTCG-3')(SEQ ID NO:6). The PCR products were cloned into pCR2.1-TOPO using TOPO TA Cloning kit (Invitrogen Life Technolgies, Carlsbad, Calif.) and the sequence of the constant regions were verified.

The KD5 variable region genes were amplified by RT-PCR from KD5 hybridoma mRNA and cloned into pCR2.1-TOPO using the heavy and light chain variable region primer mixes from Amersham-Pharmacia Biotech (Piscataway, N.J.). The variable heavy chain gene was PCR amplified using the pCR2.1-TOPO cloned variable region as template with the primers 5' BspMI/KD5VH N-term (5'-GAGAGTACCTGCGTCATGCAGATGTGAAACTGCAGGAGTCTGGCCCT-3')(SEQ ID NO:7) and 3' BspMI/KD5VH C-term (5'-GAGAGACCTGCGTCAGCTGAGGAGACGGTGACCGTGGT-3')(SEQ ID NO:8), digested with BspMI and ligated to the BsaI-digested IgG2a constant heavy gene PCR fragment amplified with the primers 5' BsaI/CH2a N-term (5'-GAGAGGGTCTCACAGCCAAAACAACAGCCCCATG-3')(SEQ ID NO:9) and 3' BsaI/CH2a C-term (5'-GAGAGGGTCTCCGGCCGCTCATTTACCCGGAGTCCGGGAGAA-3')(SEQ ID NO:10). This fragment was then ligated into the BspMI and NotI sites of pRG882. The resulting plasmid, pTE317, was capable of expressing the KD5 recombinant heavy chain gene, fused to the mROR1 signal sequence, from the CMV-MIE promoter. The variable light chain gene was PCR amplified using the pCR2.1-TOPO cloned variable region as template with the primers 5' BsmBI/KD5VL N-term (5'-GAGAGCGTCTCATGCAGACATCCAGATGACCCAGTCTCCA-3')(SEQ ID NO:11) and 3' BsmBI/KD5VL C-term (5'-GAGAGCGTCTCACAGCCCGTTTTATTTCCAGCTTGGTCCC-3')(SEQ ID NO:12), digested with BsmBI and ligated to the BsaI-digested kappa constant light gene PCR fragment amplified with the primers 5' BsaI/CLK N-term (5'-GAGAGGGTCTCAGCTGATGCTGCACCAACTGTATCC-3')(SEQ ID NO:13 ) and 3' BsaI/CLK C-term (5'-GAGAGGGTCTCAGGCCGCTCAACTCTCCCCTGTTGAACTCTTGAC-3')(SEQ ID NO:14). This fragment was then ligated into the BspMI and NotI sites of pRG882. The resulting plasmid, pTE316, was capable of expressing the KD5 recombinant light chain gene, fused to the mROR1 signal sequence, from the CMV-MIE promoter.

The 1450 bp EcoRI-NotI fragment from pTE317, encoding the KD5 heavy chain gene, was cloned into the EcoRI and NotI sites of pRG980, a vector that confers resistance to hygromycin and allows expression of recombinant genes for the UbC promoter, to yield plasmid pTE322. Similarly, the 750 bp EcoRI-NotI fragment from pTE316, encoding the KD5 light chain gene, was cloned into the EcoRI and NotI sites of pRG985, a vector that confers resistance to puromycin and allows expression of recombinant genes for the UbC promoter, to yield plasmid pTE324.

RGC10 cells (5×10$^6$) were transfected with 3 μg pTE322 and 3 μg pTE322 and selected for integration of the plasmids by growth in F12 medium supplemented with 10% fetal calf serum with 20 μg puromycin and 400 μg/ml hygromycin for 14 days. Expression of hFcγRI was induced by the addition of 1 μg/ml of doxycycline to the culture medium for three days. Double-resistant cells were incubated with 1 mg/ml rabbit IgG for eighteen hours prior to staining with goat polyclonal FITC-conjugated anti-mouse IgG (Fcγ) F (ab')$_2$ fragment (Jackson ImmunoResearch Laboratories, West Grove, Pa.). Cells were stained for 1 hour then washed twice with PBS prior to analysis by flow cytometry. The most fluorescent cells (top 5%) were isolated as a pool and expanded for 10 days, after which the protocol was repeated but the top 1% most fluorescent cells were isolated as a pool. This pool was expanded for 10 days then the top 0.1% most fluorescent cells were isolated as single cells into 96-well plates. Clones were analyzed by ELISA for expression of antibody and seven clones were chosen from 53 clones analyzed. The average specific productivity of these clones was 35 pg/cell/day and the best clone expressed the recombinant KD5 monoclonal antibody at 54 pg/cell/day.

Although the foregoing invention has been described in some detail by way of illustration and example, it will be readily apparent to those of ordinary skill in the art that certain changes and modifications may be made to the teachings of the invention without departing from the spirit or scope of the appended claims.

What is claimed is:

1. A method of detecting and/or isolating a eukaryotic cell that produces a secreted protein of interest (POI), comprising:
   (a) providing a cell comprising a nucleic acid that encodes a secreted POI and a nucleic acid that encodes a cell surface capture molecule capable of binding the POI, wherein the nucleic acid encoding the secreted POI or the nucleic acid encoding the cell surface capture molecule, or both, are transfected into the cell;
   (b) culturing the cell under conditions in which the POI and cell surface capture molecule are expressed, and a POI-capture molecule complex is formed intracellularly and displayed on the cell surface;
   (c) contacting the cell with a detection molecule, which binds to the POI displayed by the cell; and
   (d) detecting and/or isolating the cell due to it being bound to the detection molecule.

2. The method of claim 1, wherein the providing step comprises transfecting the nucleic acid encoding the secreted POI and the nucleic acid encoding the cell surface capture molecule into the cell.

3. The method of claim 1, wherein the cell is detected in step (d) by flow cytometry.

4. The method of claim 1, wherein the detection molecule is linked to a solid support or particle.

5. The method of claim 1, performed on a population of cells, wherein the isolating step isolates the cells binding to the detection molecule from the population.

6. The method claim 5, wherein the cells of the population express different levels of the POI, and the isolating step isolates cells based on relative expression level of the POI.

7. The method of claim 5, wherein the cells of the population express different POIs.

8. The method of claim 5, further comprising contacting the cells of the population with a blocking molecule that binds the cell surface capture molecule or the POI to block the diffusion of secreted POI between cells.

9. The method of claim 2, wherein the nucleic acid encoding the secreted POI is transfected into the cell before the nucleic acid encoding the cell surface capture protein and the step (a) is performed before step (b).

10. The method of claim 2, wherein the nucleic acid encoding the cell surface capture protein is transfected into the cell before the nucleic acid encoding the secreted POI.

11. The method of claim 2, wherein the nucleic acid encoding the cell surface capture protein and the nucleic acid encoding the secreted POI are transfected into the cell simultaneously.

12. The method of claim 1, wherein the protein of interest (POI) comprises an Fc domain.

13. The method of claim 12, wherein the POI is an antibody, an Fab, a single chain antibody (ScFv) or fragment thereof, or a molecule fused to an antibody constant region.

14. The method of claim 13, wherein the antibody is selected from the group consisting of IgM, IgG, IgA, IgD, and IgE, and their subtypes.

15. The method of claim 12, wherein when the POI is a ligand, the cell surface capture molecule is a receptor for the ligand; when the POI is a receptor, the cell surface capture molecule is the ligand for that receptor; when the POI is a protein or peptide, the cell surface capture molecule is an antibody specific to the POI; or when the POI is an antibody, the cell surface capture molecule is an antibody-binding protein.

16. The method of claim 15, wherein the antibody binding protein is an Fc receptor, an anti-immunoglobulin antibody, an anti-immunoglobulin ScFv, Protein A, Protein G, or functional fragments thereof.

17. The method of claim 15, wherein the secreted POI-cell surface capture molecule is selected from the group consisting of Tie1-Ang1, Tie2 -Ang2,VEGFRI-VEGF and VEGFRII-VEGF.

18. The method of claim 1, wherein the capture molecule is a protein capable of binding the POI, and has a signal sequence and membrane anchor such that the protein remains anchored in a membrane of the cell, exposed to the outside of the cell, and functions as the cell surface capture molecule.

19. The method of claim 18, wherein the membrane anchor is a transmembrane anchor or a GPI link.

20. The method of claim 19, wherein the membrane anchor is native to the cell, recombinant, or synthetic.

21. The method of claim 1, wherein the eukaryotic cell is a mammalian cell.

22. The method of claim 21, wherein the mammalian cell is a CHO cell.

23. The method of claim 21, wherein the mammalian cell is an antibody-producing cell fused to an immortalized cell.

24. The method of claim 23, wherein the antibody-producing cell is a B-cell or derivative thereof.

25. The method of claim 24, wherein the B-cell derivative is a plasma cell, a hybridoma, a myeloma, or a recombinant cell.

26. A method of detecting and isolating a eukaryotic cell that produces a secreted protein of interest (POI), comprising:
   (a) transfecting the cell with a nucleic acid that encodes a cell surface capture molecule capable of binding the POI;
   (b) culturing the cell under conditions in which a POI-cell surface capture molecule complex is formed intracellularly and expressed on the cell surface;
   (c) contacting the cell with a detection molecule capable of binding the POI, wherein the surface-displayed POI is detected; and
   (d) isolating the detected cell.

27. The method of claim 26, wherein when the POI is a ligand, the cell surface capture molecule is a receptor for the ligand; when the POI is a soluble receptor, the cell surface capture molecule is the ligand for that receptor; when the POI is a growth factor, the cell surface capture molecule is a protein capable of binding the growth factor; or when the POI is an antibody, the cell surface capture molecule is an antibody-binding protein.

28. The method of claim 27, wherein the antibody is selected from the group consisting of IgM, IgG, IgA, IgD or IgE, as well as their subtypes.

29. The method of claim 27, wherein the antibody binding protein is an Fc receptor, an anti-immunoglobulin antibody, an anti-immunoglobulin ScFv, Protein A, Protein G, or functional fragments thereof.

30. The method of claim 26, wherein the eukaryotic cell is a mammalian cell.

31. The method of claim 30, wherein the mammalian cell is a CHO cell.

32. The method of claim 30, wherein the mammalian cell is an antibody-producing cell fused to an immortalized cell.

33. The method of claim 32, wherein the antibody-producing cell is a B-cell or derivative thereof.

34. The method of claim 33, wherein the B-cell derivative is a plasma cell, a hybridoma, a myeloma, or a recombinant cell.

35. A method of detecting and isolating a eukaryotic cell that produces a secreted protein of interest (POI), comprising:
   (a) transfecting a cell with a nucleic acid molecule that encodes a secreted POI comprising an Fc domain;
   (b) transfecting the cell with a nucleic acid molecule that encodes a cell surface capture molecule capable of binding an Fc domain;
   (c) culturing the cell under conditions in which a POI-cell surface capture molecule complex is expressed on the cell surface;
   (d) contacting the cell with a detection molecule capable of binding the POI, wherein the surface-displayed POI is detected;
   (e) isolating the detected cell.

36. The method of claim 35, wherein the eukaryotic cell is a mammalian cell.

37. The method of claim 36, wherein the mammalian cell is a CHO cell.

38. The method of claim 37, wherein the mammalian cell is an antibody-producing cell fused to an immortalized cell.

39. The method of claim 38, wherein the antibody-producing cell is a B-cell or derivative thereof.

40. The method of claim 39, wherein the B-cell derivative is a plasma cell, a hybridoma, a myeloma, or a recombinant cell.

41. The method of claim 35, wherein the protein of interest is an antibody, an Fab, a single chain antibody (ScFv), or a fragment thereof.

42. The method of claim 41, wherein the antibody is selected from the group consisting of IgM, IgG, IgA, IgD or IgE.

43. The method of claim 42, wherein the cell surface capture molecule is an Fc receptor, Protein G, or functional fragment thereof capable of binding an Fc domain.

44. The method of claim 35, wherein the detection molecule comprises two molecules that bind each other and are differentially labeled.

45. The method of claim 35, further comprising following step (c), (c') contacting the cell with a blocking molecule capable of binding the cell surface capture molecule or POI.

46. The method of claim 35, wherein the method is conducted in a high viscosity medium.

47. The method of claim 35, wherein the POI-capture molecule complex forms intracellularly.

* * * * *